(12) United States Patent
Koren et al.

(10) Patent No.: US 10,098,975 B2
(45) Date of Patent: Oct. 16, 2018

(54) LABELED PKG-1-ALPHA-BINDING COMPOUNDS AND THEIR USE IN IMAGING AND QUANTIFYING PAIN

(71) Applicant: THE TRUSTEES OF COLUMBIA UNIVERSITY IN THE CITY OF NEW YORK, New York, NY (US)

(72) Inventors: Andrei O. Koren, Bethany, CT (US); Shi-Xian Deng, White Plains, NY (US); Donald W. Landry, New York, NY (US); Chaitanya Divgi, Meadowbrook, PA (US)

(73) Assignee: THE TRUSTEES OF COLUMBIA UNIVERSITY IN THE CITY OF NEW YORK, New York, NY (US)

( * ) Notice: Subject to any disclaimer, the term of this patent is extended or adjusted under 35 U.S.C. 154(b) by 0 days.

(21) Appl. No.: 14/757,817

(22) Filed: Dec. 23, 2015

(65) Prior Publication Data
US 2016/0243266 A1 Aug. 25, 2016

Related U.S. Application Data

(63) Continuation of application No. PCT/US2014/044115, filed on Jun. 25, 2014.

(60) Provisional application No. 61/839,649, filed on Jun. 26, 2013.

(51) Int. Cl.
| | |
|---|---|
| *A61K 51/00* | (2006.01) |
| *A61M 36/14* | (2006.01) |
| *A61K 51/04* | (2006.01) |
| *C07B 59/00* | (2006.01) |
| *C07D 403/12* | (2006.01) |

(52) U.S. Cl.
CPC ........ *A61K 51/0453* (2013.01); *C07B 59/002* (2013.01); *C07D 403/12* (2013.01); *A61K 51/044* (2013.01); *C07B 2200/05* (2013.01)

(58) Field of Classification Search
None
See application file for complete search history.

(56) References Cited

U.S. PATENT DOCUMENTS

| | | |
|---|---|---|
| 3,981,769 A | 9/1976 | Winchell et al. |
| 5,169,942 A | 12/1992 | Johnson et al. |
| 5,264,570 A | 11/1993 | Johnson et al. |
| 8,309,055 B2 | 11/2012 | Arstad et al. |
| 2008/0176920 A1 | 7/2008 | Ambron et al. |
| 2011/0077430 A1 | 3/2011 | Yu et al. |

OTHER PUBLICATIONS

Behera et al. (J. Nucl. Med. 2011, 52, 1308-1312).*
Jones et al. (Eur. J. Pain 2004, 8, 479-485).*
Andres et al. "Synthesis, in Vivo Occupancy, and Radiolabeling of Potent Phosphodiesterase Subtype-10 Inhibitors as Candidates for Positron Emission Tomography Imaging", J. Med. Chem. 54, 5820-5835. (2011).
Behera et al. "18F-FDG PET/MRI Can Be Used to Identify Injured Peripheral Nerves in a Model of Neuropathic Pain," J Nucl Med. 52, 1308-1312. (2011).
Caraceni et al., "Cancer pain management and palliative care," Handbook of Clinical Neurology; 104(3rd series): 391-415 (2012).
Centers for Disease Control and Prevention. 2011. Policy Impact: Prescription Painkiller Overdoses. Atlanta, GA: US Department of Health and Human Services, CDC. Available at http://www.cdc.gov/homeandrecreationalsafety/rxbrief/index.html. Accessed Apr. 12, 2016.
Centers for Disease Control and Prevention. 2011. Vital Signs: Overdoses of Prescription Opioid Pain Relievers—United States, 1999-2008. Morbidity and Mortality Weekly Report 60:1487-1492. Available at http://www.cdc.gov/mmwr/pdf/wk/mm6043.pdf. Accessed (Nov. 4, 2011) Accessed on Apr. 12, 2016.
Centers for Disease Control and Prevention. 2012. CDC Grand Rounds: Prescription Drug Overdoses—a U.S. Epidemic. Morbidity and Mortality Weekly Report 61:10-13. Available at http://www.cdc.gov/mmwr/pdf/wk/mm6101.pdf. (Jan. 13, 2012) Accessed on Apr. 12, 2016.
Committee on Advancing Pain Research, Care, and Education, Institute of Medicine. 2011. Relieving Pain in America: A Blueprint for Transforming Prevention, Care, Education and Research. Washington, D.C.: The National Academies Press. Available at http://www.nap.edu/catalog.php?record_id=13172. Accessed on Apr. 12, 2016.
Dorsi et al., "The tibial neuroma transposition (TNT) model of neuroma pain and hyperalgesia," Pain 134, 320-334. (2008).
Frampton, "The measurement of pain," Clinical Oncology 23, 381-6. (2011).
Fuchtner et al., "Aspects of 6-[18F]fluoro-L-DOPA preparation: precursor synthesis, preparative HPLC purification and determination of radiochemical purity," Nuclear Medicine and Biology 29, 477-481. (2002).
Hølen et al., "Pain Assessment Tools: Is the Content Appropriate for Use in Palliative Care?," J Pain Symptom Management 32(6), 567-80. (2006).
Hui, et al., "Asymmetric Addition of Diethylzinc to Ketones promoted by Tartaric Acid Derivatives," Synthetic Communications, 38(14), 2374-2384. (2008).
International Search Report dated Oct. 6, 2014 in International Application No. PCT/US14/44115.
Jamison et al., "Assessment and treatment of abuse risk in opioid prescribing for chronic pain," Pain Research and Treatment 2011: Article ID 941808, 12 pages. (2011) Available at http://www.hindawi.com/journals/prt/2011/941808. Accessed on Apr. 12, 2016.
Kinahan, et al., "X-Ray Based Attenuation Correction for Positron Emission Tomography/Computed Tomography Scanners," Seminars in Nuclear Medicine. 33(3), 166-79. (2003).
Lasne et al., "Chemistry of β +—Emitting Compounds Based on Fluorine-18," Topics in Current Chemistry 222, 201-258. (2002).
Lee et al., "A Fluoride-Derived Electrophilic Late-Stage Fluorination Reagent for PET Imaging," Science 334(6056), 639-642. (2011).

(Continued)

*Primary Examiner* — Michael G Hartley
*Assistant Examiner* — Melissa J Perreira
(74) *Attorney, Agent, or Firm* — Baker Botts L.L.P.

(57) ABSTRACT

The present invention relates to the use of compounds that selectively bind to activated protein kinase G 1 alpha for imaging the anatomic basis for chronic pain. Such imaging may also be used to objectively quantify chronic pain.

4 Claims, 24 Drawing Sheets

(56) References Cited

OTHER PUBLICATIONS

Figure 1A:
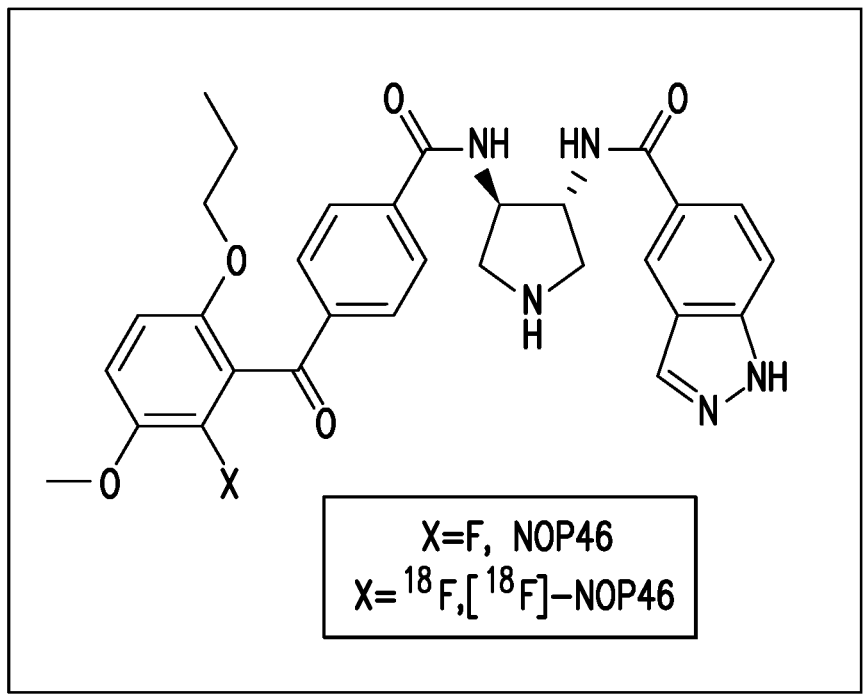

Littich et al., "Novel Strategies for Fluorine-18 Radiochemistry," Angewandte Chemie International Edition 51, 1106-1109. (2012).
Montazeri, "Quality of life data as prognostic indicators of survival in cancer patients: an overview of the literature from 1982 to 2008," Health and Quality of Life Outcomes 7, 102-23. (2009).
Nehmeh et al., "Effect of respiratory gating on reducing lung motion artifacts in PET imaging of lung cancer," Med Phys 29(3), 366-71. (2002).
Pasero et al., 1999. Pain: Clinical Manual. St. Louis: Mosby (Table of Contents).
Portenoy, "Treatment of cancer pain," Lancet 377, 2236-47. (2011).
Raphael et al., "Cancer Pain: Part 1: Pathophysiology; Oncological, Pharmacological, and Psychological Treatments: A Perspective from the British Pain Society Endorsed by the UK Association of Palliative Medicine and the Royal College of General Practitioners," Pain Med 11, 742-764. (2010).
Setani et al., "Comparison of Different Methods for Attenuation Correction in Brain PET: Influence on the Calculation of the Metabolic Glucose Rate," Nuklearmedizin. 39, 50-5. (2000).
Sherman et al., "Thermography in Pain Management," Practical Pain Management, Available at http://www.practicalpainmanagement.com/resources/diagnostic-tests/thermography-pain-management. 2004. Accessed Apr. 12, 2016.
Song, "Heterogeneous Pd-Catalyzed Asymmetric Allylic Substitution Using Resin—Supported Trost-Type Bisphosphane Ligands," Angewandte Chemie, International Edition 41(20), 3852-3854. (2002).
Sung et al., "Activation and Retrograde Transport of Protein Kinase G in Rat Nociceptive Neurons After Nerve Injury and Inflammation," Neuroscience 141(2), 697-709. (2006).
Sung et al., "Pathways that elicit long-term changes in gene expression in nociceptive neurons following nerve injury: contributions to neuropathic pain," Neurological Research 26(2), 195-203. (2004).
Teare et al., "Radiosynthesis and Evaluation of [18F]Selectfluor bis(triflate)," Angewandte Chemie International Edition 49, 6821-6824. (2010).
Van Elmpt et al., "Optimal gating compared to 3D and 4D PET reconstruction for characterization of lung tumours," Eur J Nucl Med Mol Imaging 38, 843-855. (2011).
Varrone et al., "EANM procedure guidelines for PET brain imaging using [18F]FDG, version 2," Eur J Nucl Med Mol Imaging 36(12), 2103-10. (2009).
Voscopoulos, et al., "When does acute pain become chronic?" British Journal of Anaesthesia 105 (S1): i69—i85. (2010) Available at http://bja.oxfordjournals.org/content/105/suppl_1/i69.full.pdf+html. Accessed Apr. 12, 2016.
Waxman et al., "Society of Nuclear Medicine Procedure Guideline for FDG PET Brain Imaging: Version 1.0, approved Feb. 8, 2009," pp. 1-12. Available for free download on the internet: http://interactive.snm.org/docs/Society%20of%20Nuclear%20Medicine%20Procedure20Guideline%20for%20FDG%20PET%20Brain%20Imaging.pdf Accessed Apr. 12, 2016.
I. Tracey, "Imaging pain," British Journal of Anaesthesia, 101(1):32-39 (2008).
Supplementary European Search Report dated Jan. 4, 2017 in Application No. 14818293.

\* cited by examiner

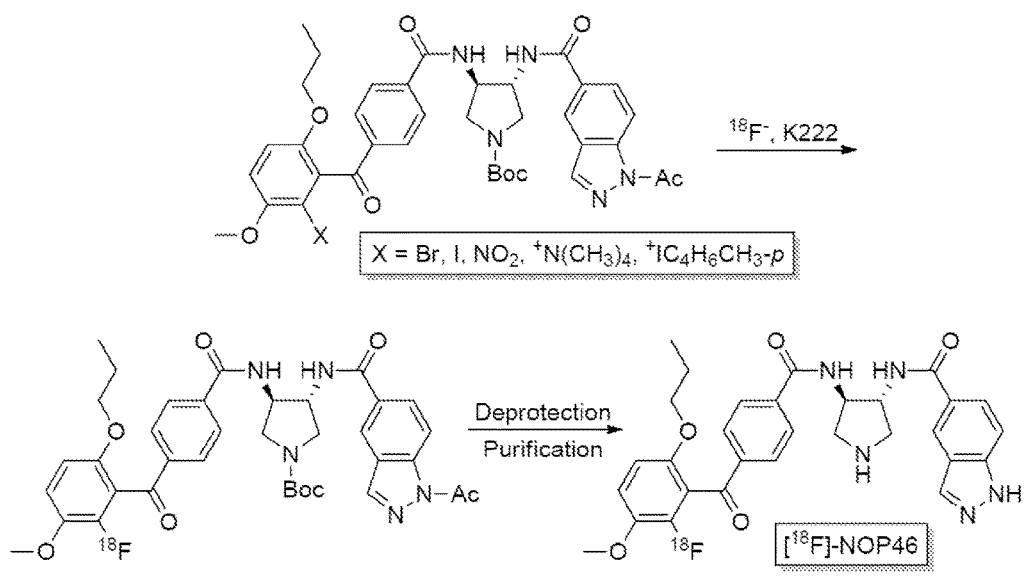

FIG. 7A
NOP1
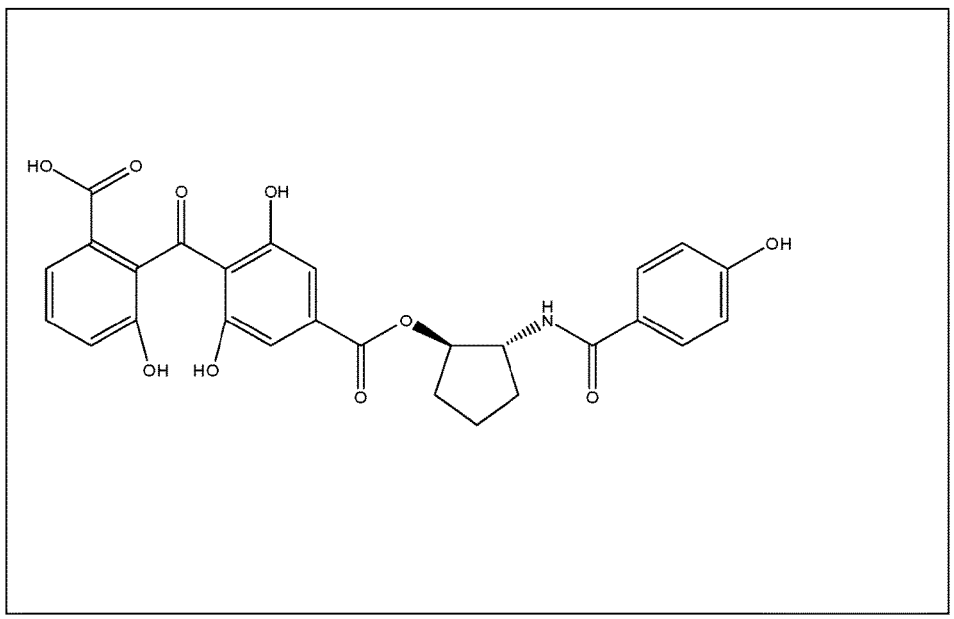
NOP2
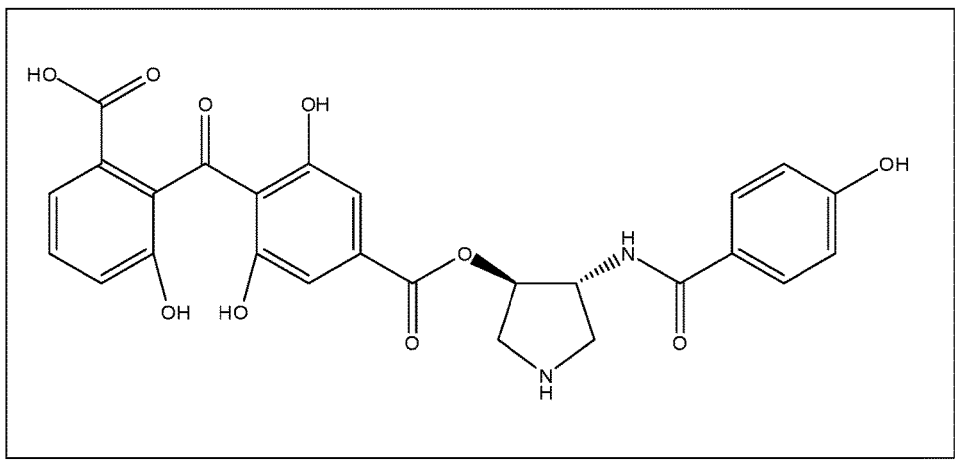

FIG. 7A continued
NOP6
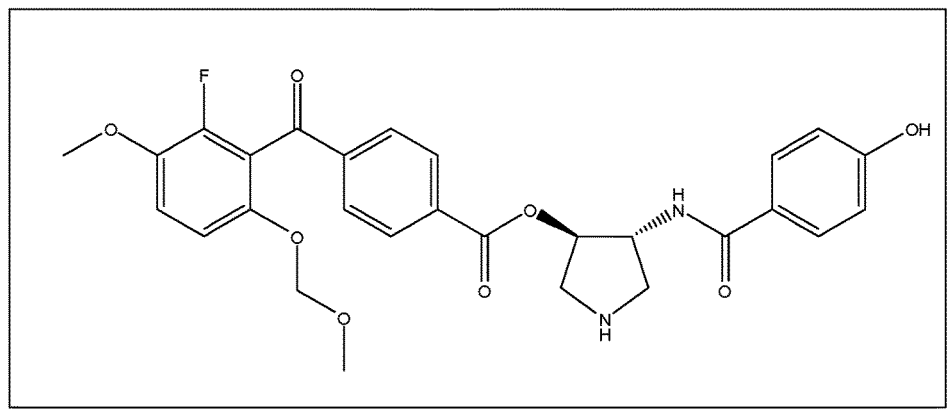
NOP7
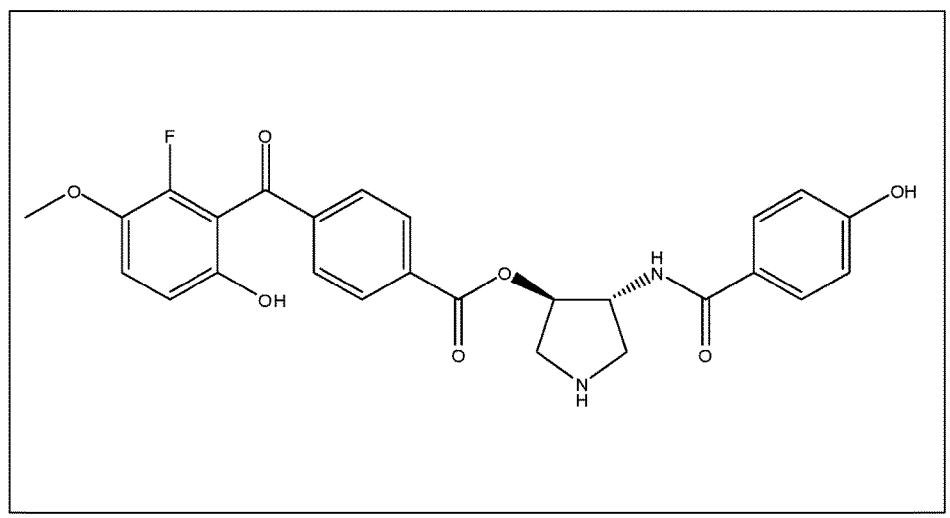

FIG. 7A continued
NOP10
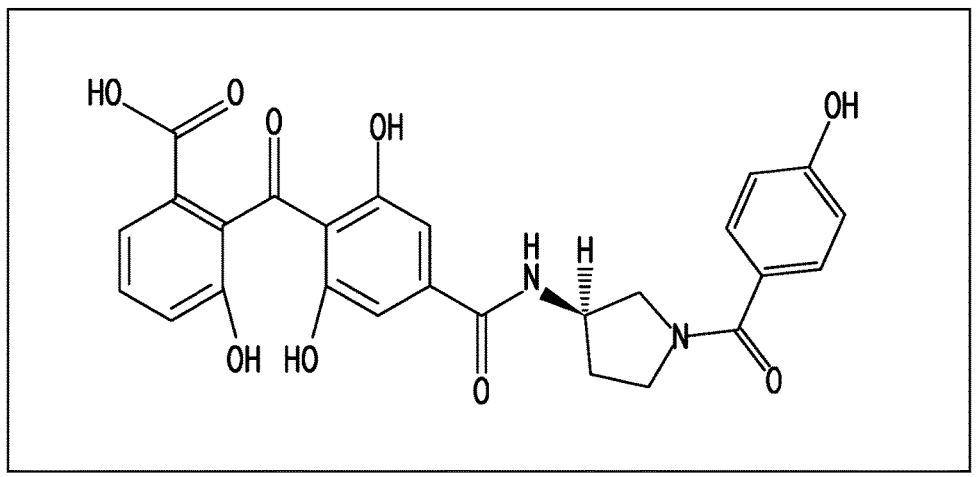
NOP15
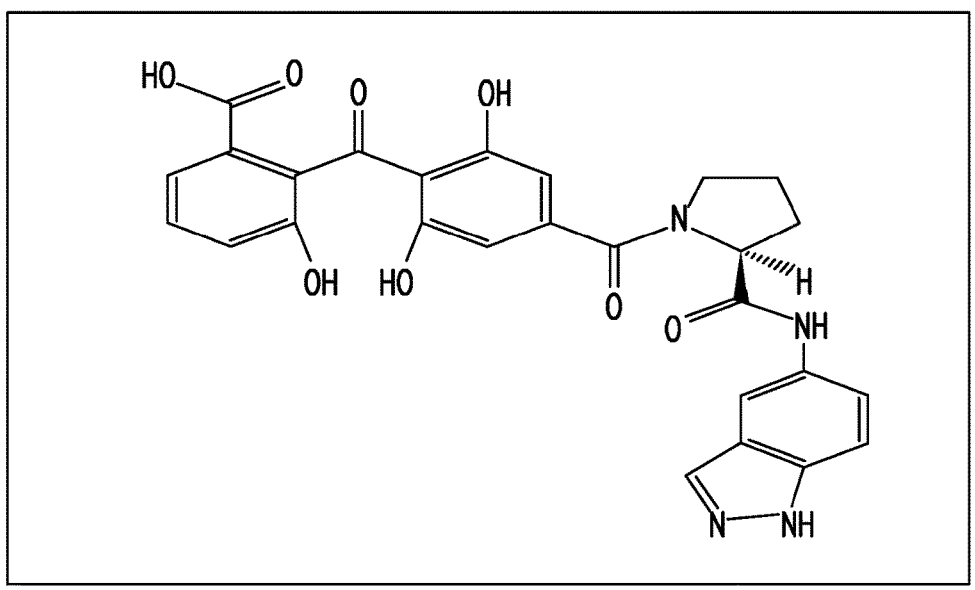

FIG. 7A continued
NOP21
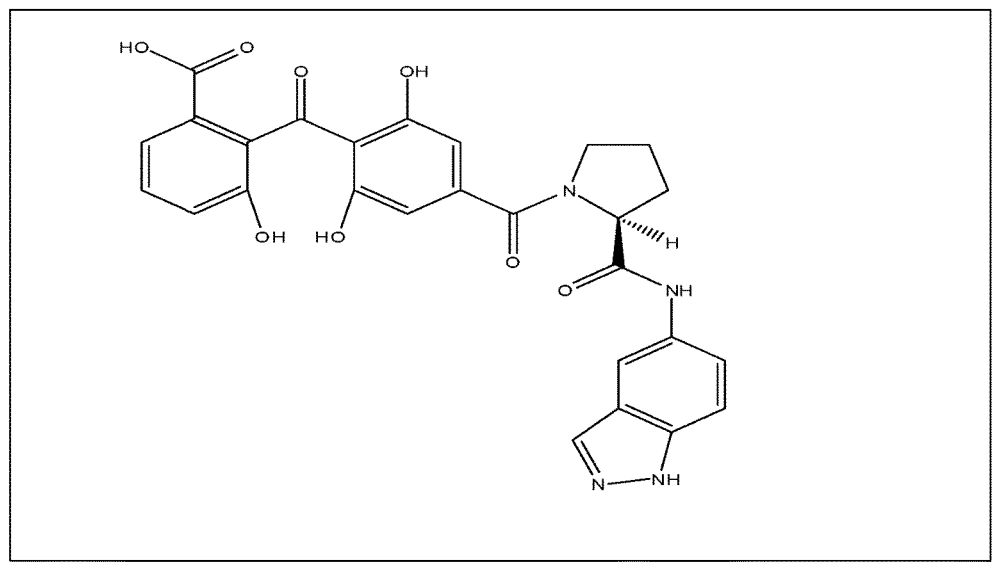
NOP22
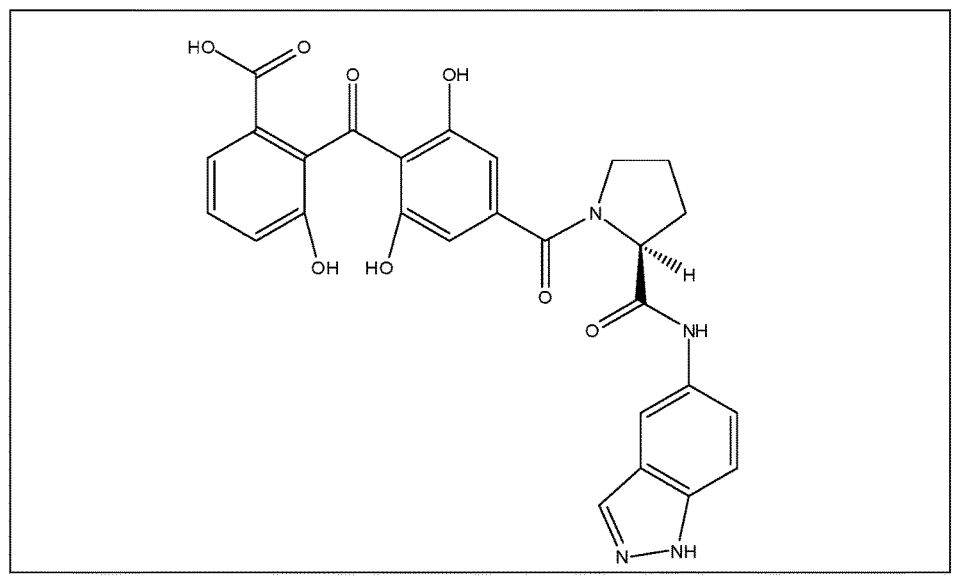

FIG. 7A continued
NOP44
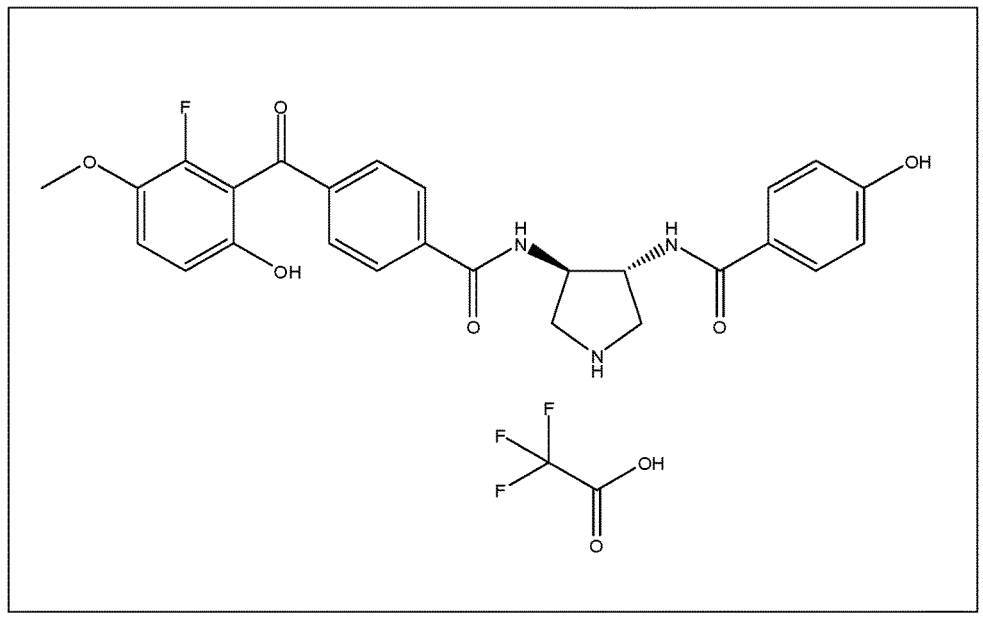
NOP45
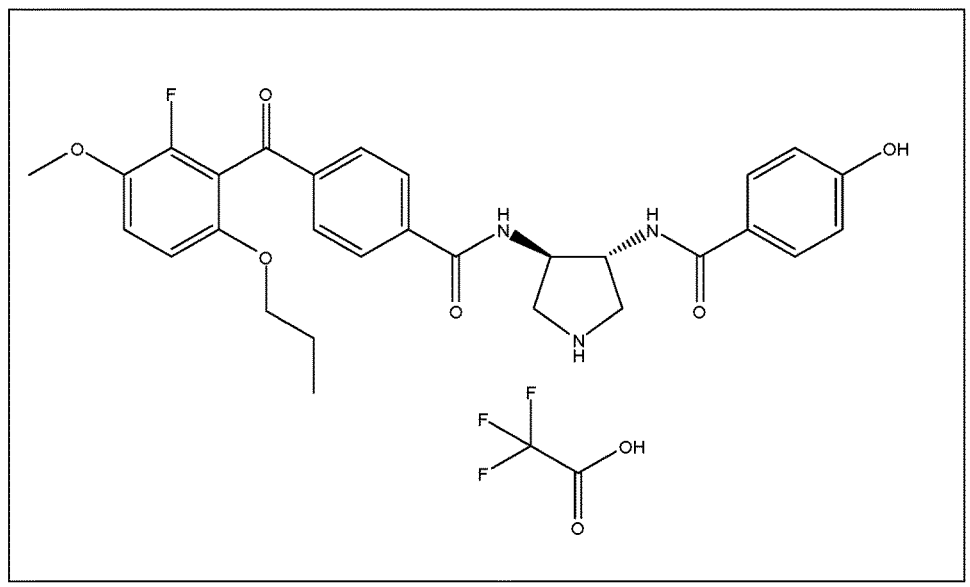

FIG. 7A continued
NOP55
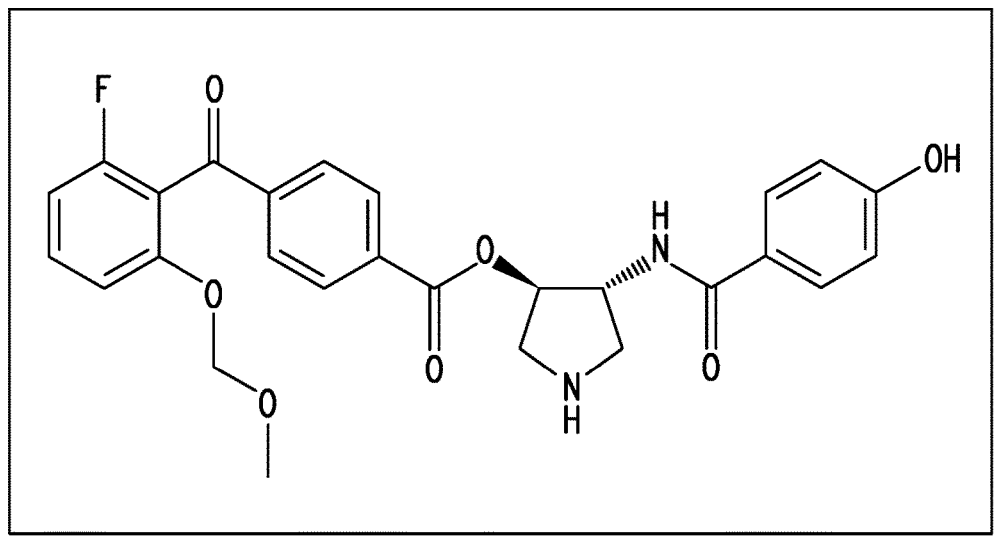
NOP69
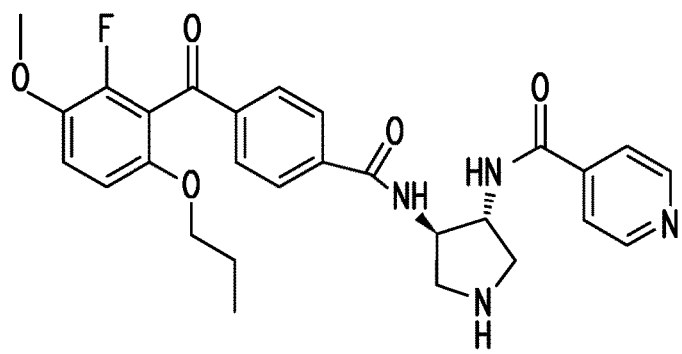

Figure 7B:
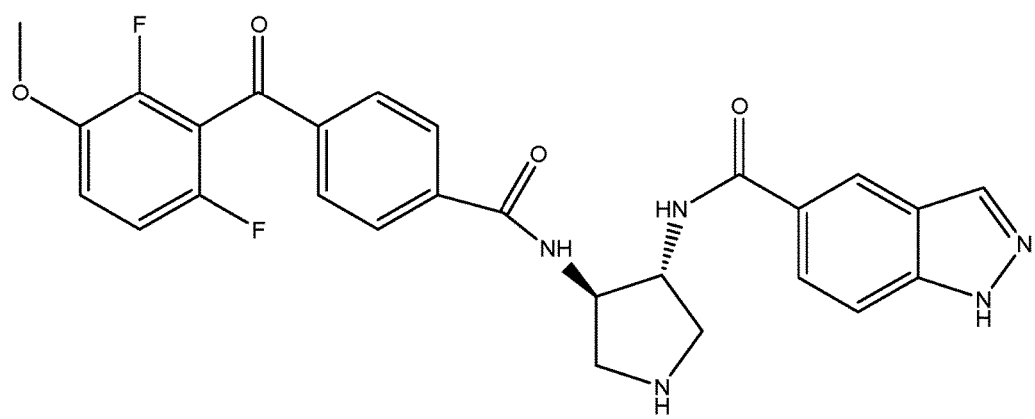

FIG. 7B
NOP35
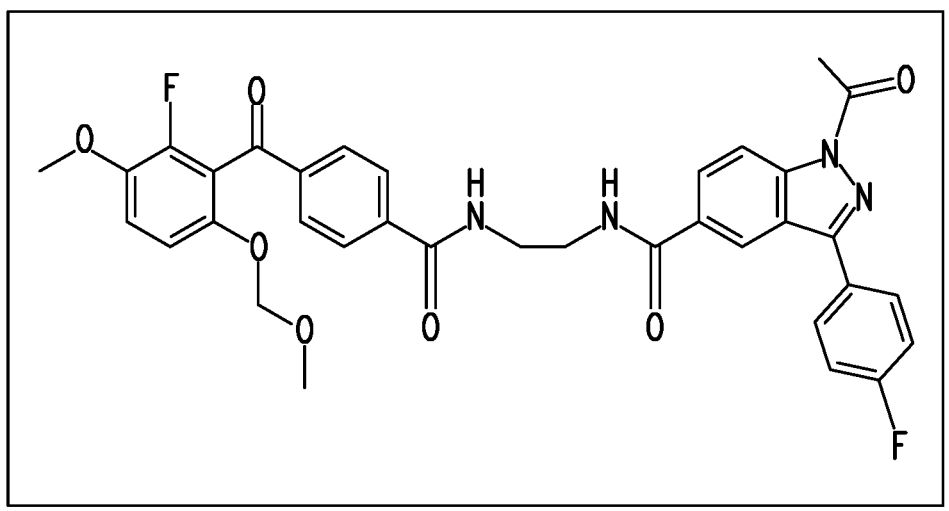
NOP47
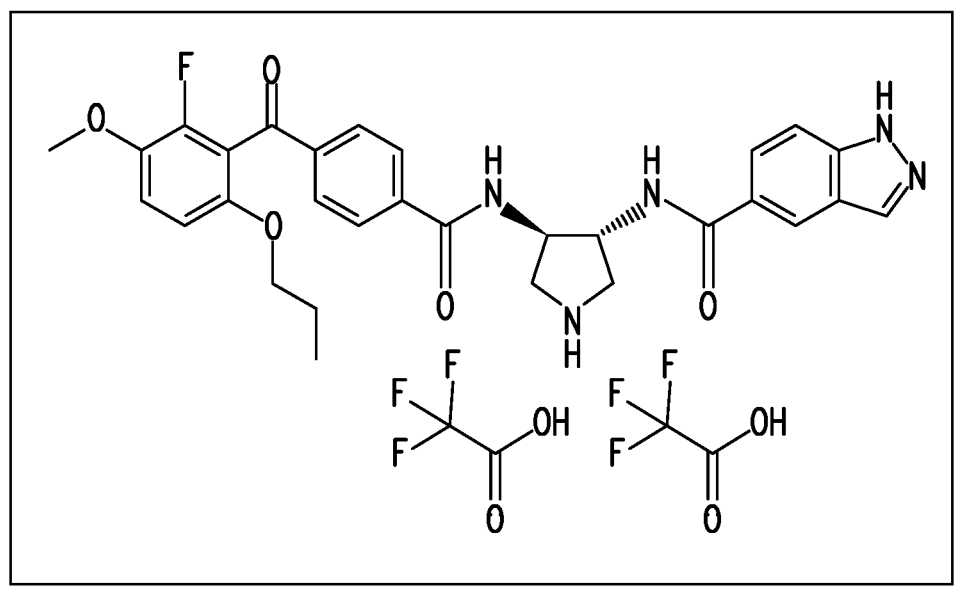

FIG. 7B continued
NOP50
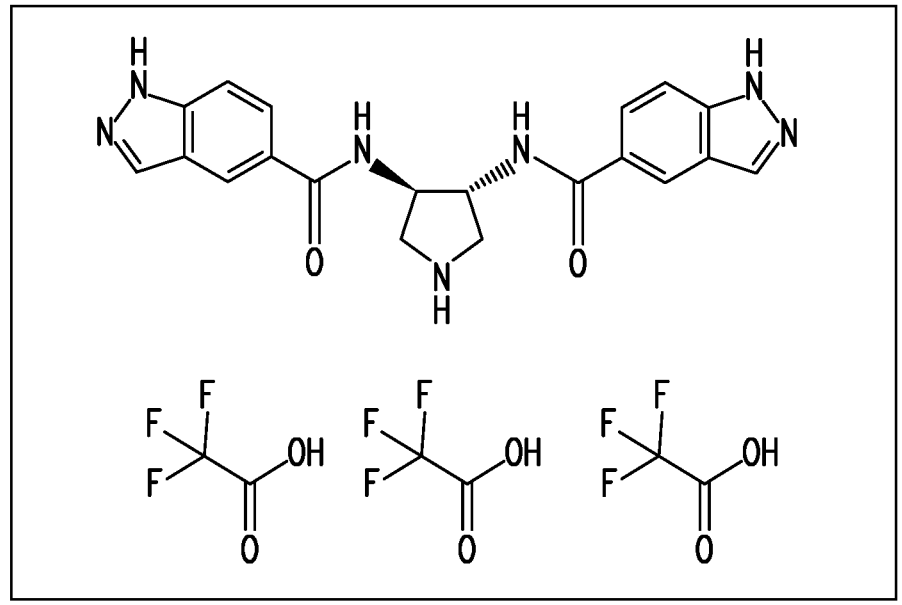
NOP51
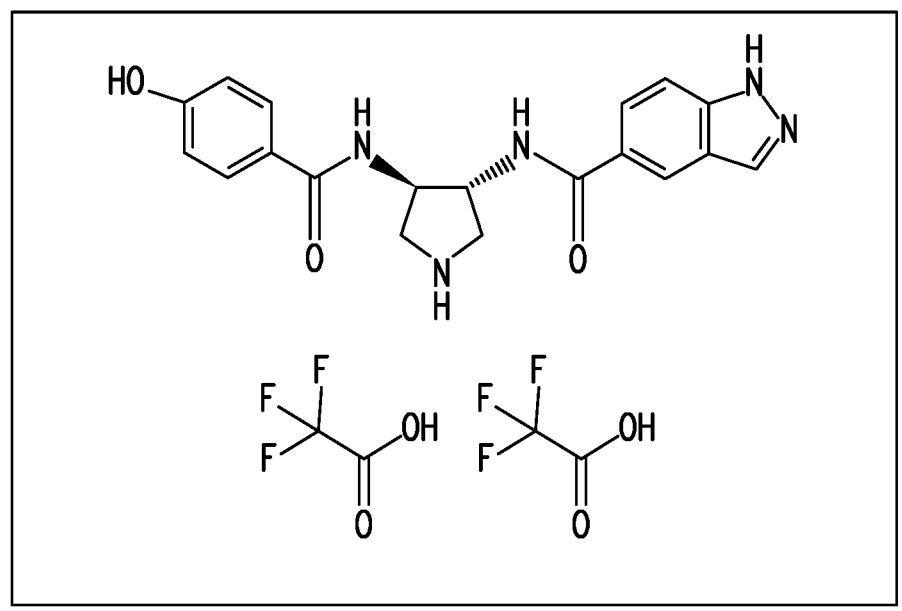

FIG. 7B continued
NOP53
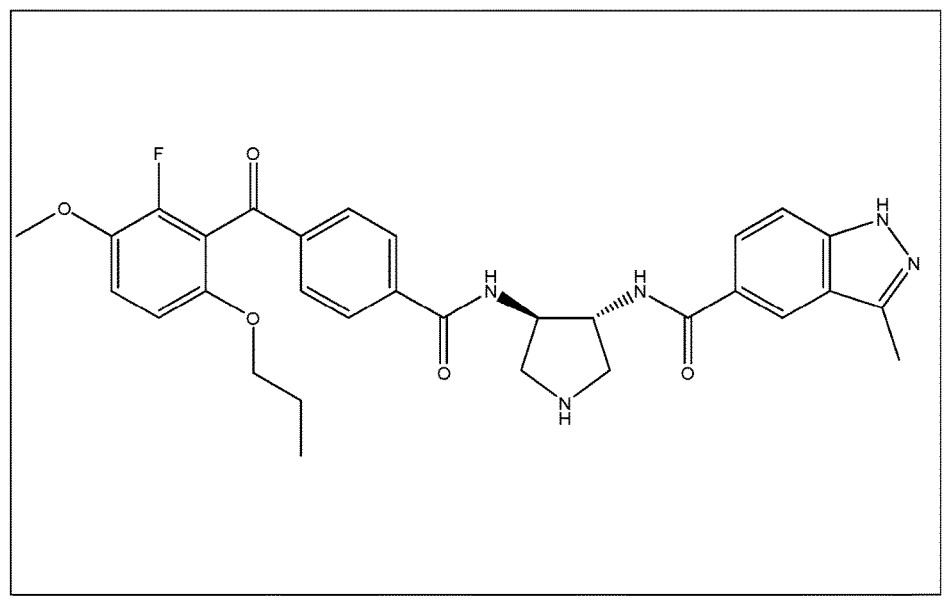
NOP56
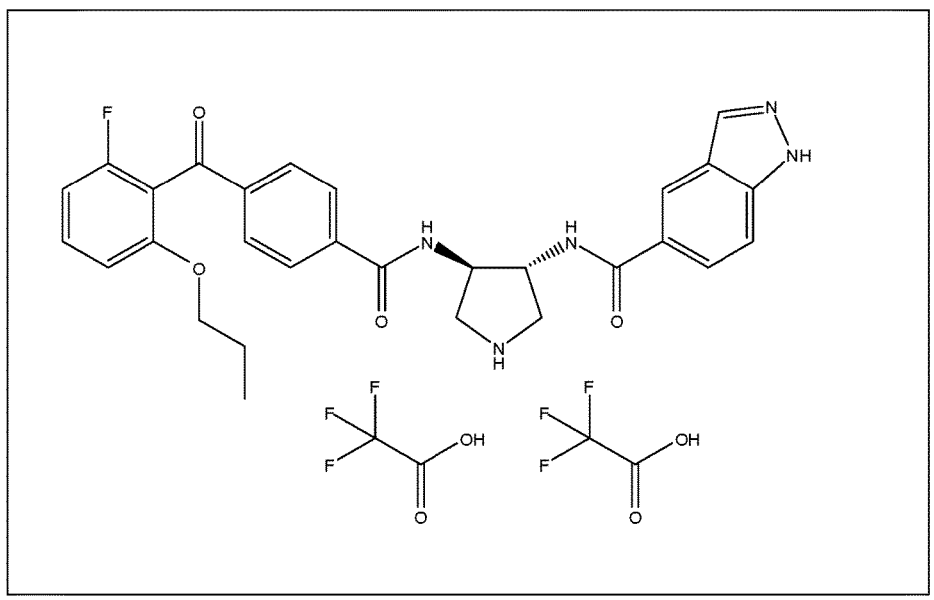

FIG. 7B continued
NOP58
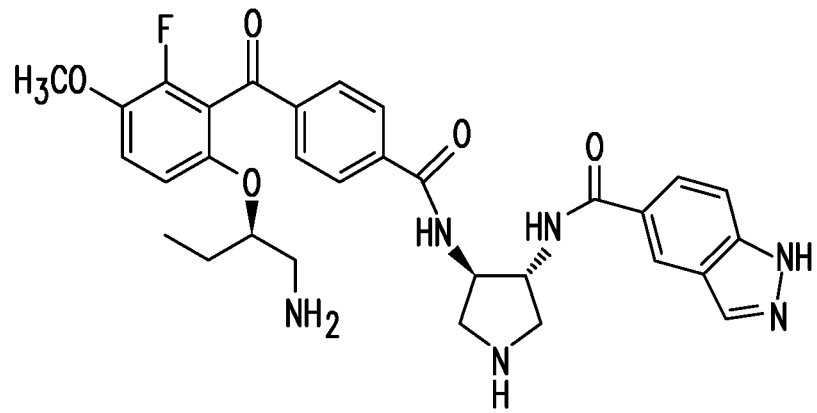
NOP59
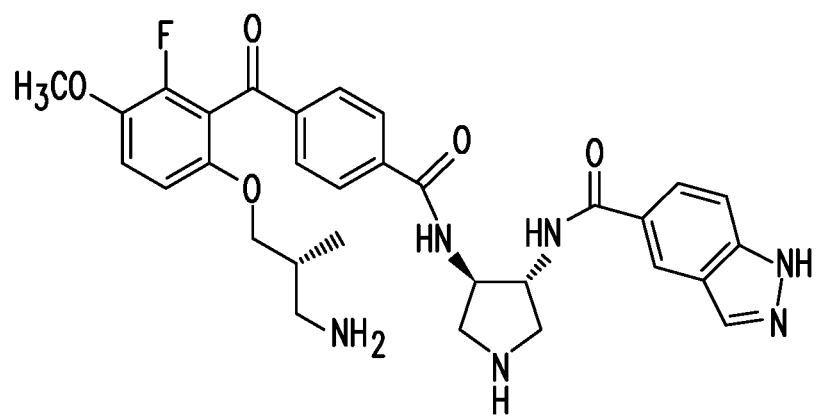

FIG. 7B continued
NOP60
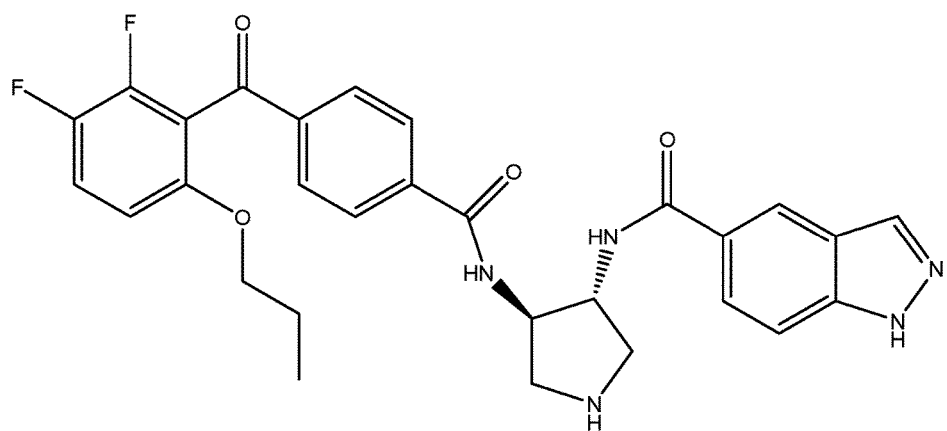
NOP61
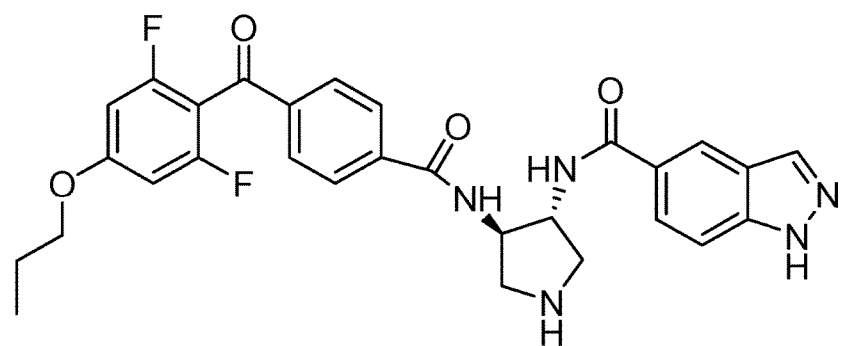

FIG. 7B continued
NOP62
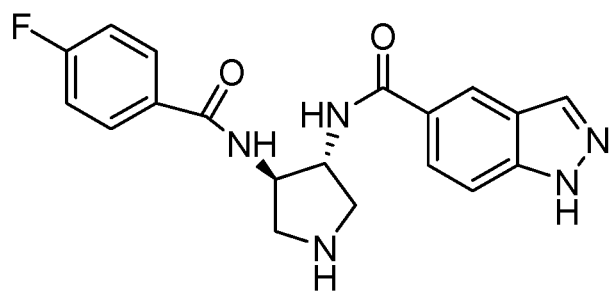
NOP63
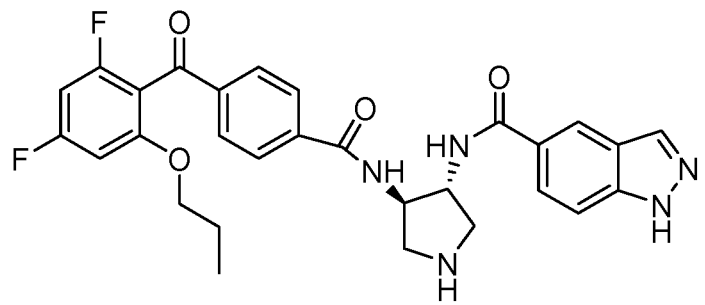
NOP67
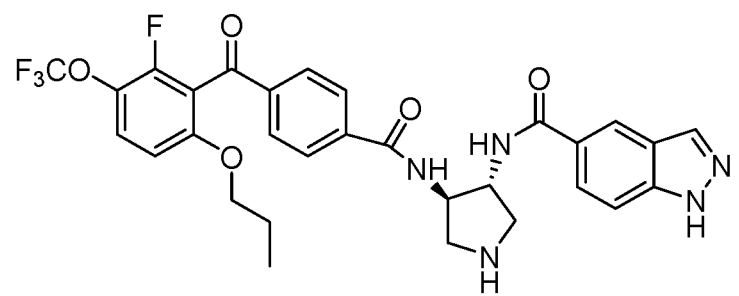

NOP72

LABELED PKG-1-ALPHA-BINDING COMPOUNDS AND THEIR USE IN IMAGING AND QUANTIFYING PAIN

PRIORITY CLAIM

This application is a continuation of International Patent Application No. PCT/US2014/044115, filed on Jun. 25, 2014, and claims priority to U.S. Provisional Application No. 61/839,649, filed Jun. 26, 2013, to both of which priority is claimed and the contents of both of which are incorporated herein in their entireties.

1. INTRODUCTION

The present invention relates to the use of compounds that selectively bind to activated protein kinase G 1 alpha for imaging the anatomic basis for chronic pain. Such imaging may also be used to objectively quantify chronic pain.

2. BACKGROUND OF THE INVENTION

Chronic pain is initiated in the periphery by either a nerve injury ("neuropathic pain") or an inflammation. Both sources result in pain that is a major clinical problem that has mostly resisted effective treatment. Chronic pain can result from a number of causes, including trauma (accidental or surgical), metabolic conditions such as diabetes, and cancer.

Pain is the most common underlying symptom in cancer, occurring in about half of all patients with disease [11]. The absence of pain is associated with improved quality of life and perhaps survival [12]. Neuronal or neuropathic pain, which constitutes about half of all cancer pain, may be a result of tumor compression or tissue infiltration, as well as from direct neuronal involvement [13].

Chronic pain has a neurophysiologic correlate. Protein Kinase G-1α (PKG-1α) mediates the development of many types of chronic pain. PKG-1α is activated in axons at sites of injury or inflammation and subsequently transported retrogradely to the dorsal root ganglion (DRG) where it indirectly affects gene expression, leading to a long-term hyperexcitability (LTH) [10]. The DRG is part of the peripheral nervous system but communicates directly with the central nervous system. LTH enhances the activity of pain centers for extended periods of time, which is the root cause for chronic hyperalgesia (increased sensitivity to pain) and allodynia (pain from a stimulus that does not normally provoke pain). Significantly, activated PKG-1α is present only in the DRG whose nociceptive neurons are mediating chronic pain and is absent from motor axons.

Options for treating chronic pain are usually limited to the prescription of opioid analgesics that have untoward side effects such as sedation, addiction, and risk of overdose. In 2008, approximately 100 million U.S. adults were burdened by chronic pain [4] and most had been prescribed opioid pain relievers. In addition, an increasing number of patients simulate chronic pain symptoms in an effort to obtain the painkillers [5].

Prescription drug abuse is the fastest growing drug problem in the United States [1]. In 2008, more than 20,000 deaths occurred as a result of unintentional overdose of a prescription drug [2]. Nearly 15,000 of them were caused by prescription opioid analgesics, which is more than 3 times the 4,000 people killed by these drugs in 1999 [2]. In addition, for every overdose death, related to opioid analgesics, 10 persons were admitted for substance abuse treatment, 32 visited emergency departments due to prescription painkiller misuse or abuse, 130 reported drug dependence, and 825 reported nonmedical uses of opioid analgesics [3]. In 2010, one in 20 people in the United States, ages 12 and older, used prescription painkillers nonmedically [2]. Overall, nonmedical use of prescription pain relievers costs insurance companies up to $72.5 billion annually [2]. Thus, prescription analgesics misuse and abuse is an alarming and rapidly growing problem that that needs to be addressed on various levels.

The problems of misuse and abuse of prescription analgesics stem from the current lack of means of objective detection and assessment of chronic pain. With no objective evidence of chronic pain, physicians are left to rely mainly on patient testimony in identifying whether the pain originates from the peripheral or the central nervous system (and thus requires a certain treatment strategy), in matching the type of analgesic and its dose to the intensity of the pain, and in distinguishing actual chronic pain from simulation attempts. The alarming rate of prescription analgesics misuse and abuse combined with the growing utilization of opioid painkillers in clinical settings urgently call for development of a diagnostic tool for objective assessment of chronic pain.

A family of compounds that selectively bind to a chronic pain specific, activated form of protein kinase G-1α (PKG-1α) has been identified. This family, referred to as "NOP" compounds, is disclosed in United States Patent Application Publication No. 20080176920.

3. SUMMARY OF THE INVENTION

The present invention relates to the use of compounds that selectively bind to activated PKG-1α for imaging and quantifying chronic pain. In certain non-limiting embodiments, detectably labeled activated PKG-1α ligands may be administered to a subject such that they localize in a dorsal root ganglion that mediates the sensation of chronic pain.

In certain non-limiting embodiments, the activated PKG-1α ligand is a detectably labeled NOP compound.

In specific non-limiting embodiments, the labeled NOP compound is NOP-46 or NOP-60.

In certain non-limiting embodiments, the NOP compound is labeled with the fluorine radioisotope, $[^{18}F]$.

In certain non-limiting embodiments, the NOP compound is labeled with the carbon isotope, $[^{11}C]$.

In certain non-limiting embodiment, the invention provides for a precursor for preparing a radiolabeled NOP compound ("NOP labeling precursor").

In certain non-limiting embodiments, the invention provides for a NOP46 labeling precursor comprising one or more of (a) an easily removable protecting group at the nitrogen atom of the pyrrolidine cycle; (b) an easily removable protecting group at the nitrogen atom of the indazole moiety; and/or (c) an aryl iodonium leaving group at the position intended for radiolabeling.

In one specific non-limiting embodiment, the fluorine of NOP46 is $[^{18}F]$ ("$[^{18}F]$-NOP46").

In one specific non-limiting embodiment, the carbon in the methoxy group of NOP46 is $[^{11}C]$ ("$[^{11}C]$-NOP46").

The present invention may be used to help control the widespread misuse and abuse of prescription analgesics, by identifying malingering individuals as well as, prospectively, determining optimal drug dosage in persons with chronic pain. These measures would save the healthcare industry billions of dollars, in addition to the societal costs of thousands of lives that are lost to painkiller overdoses each year.

4. BRIEF DESCRIPTION OF THE FIGURES

Figure 1B:
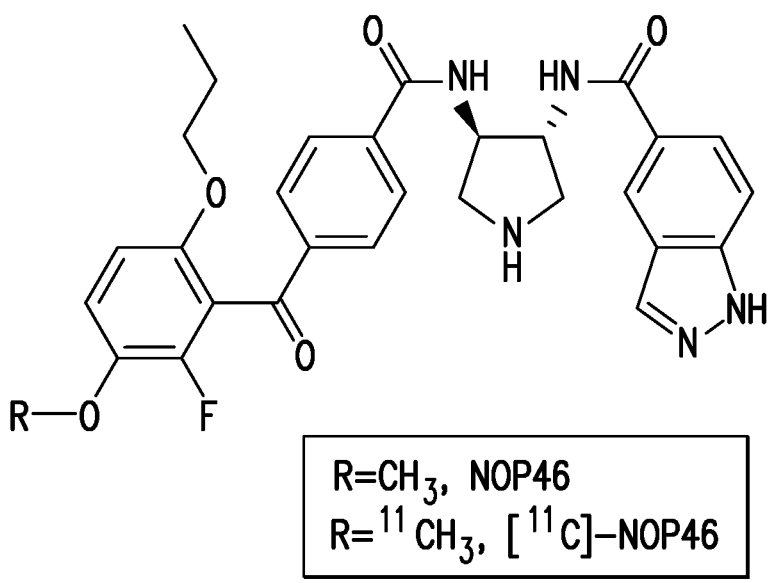

FIG. 1A-B. Chemical structures of NOP46 and (A) [$^{18}$F]-NOP46 and (B) [$^{11}$C]-NOP46.

Figure 2:
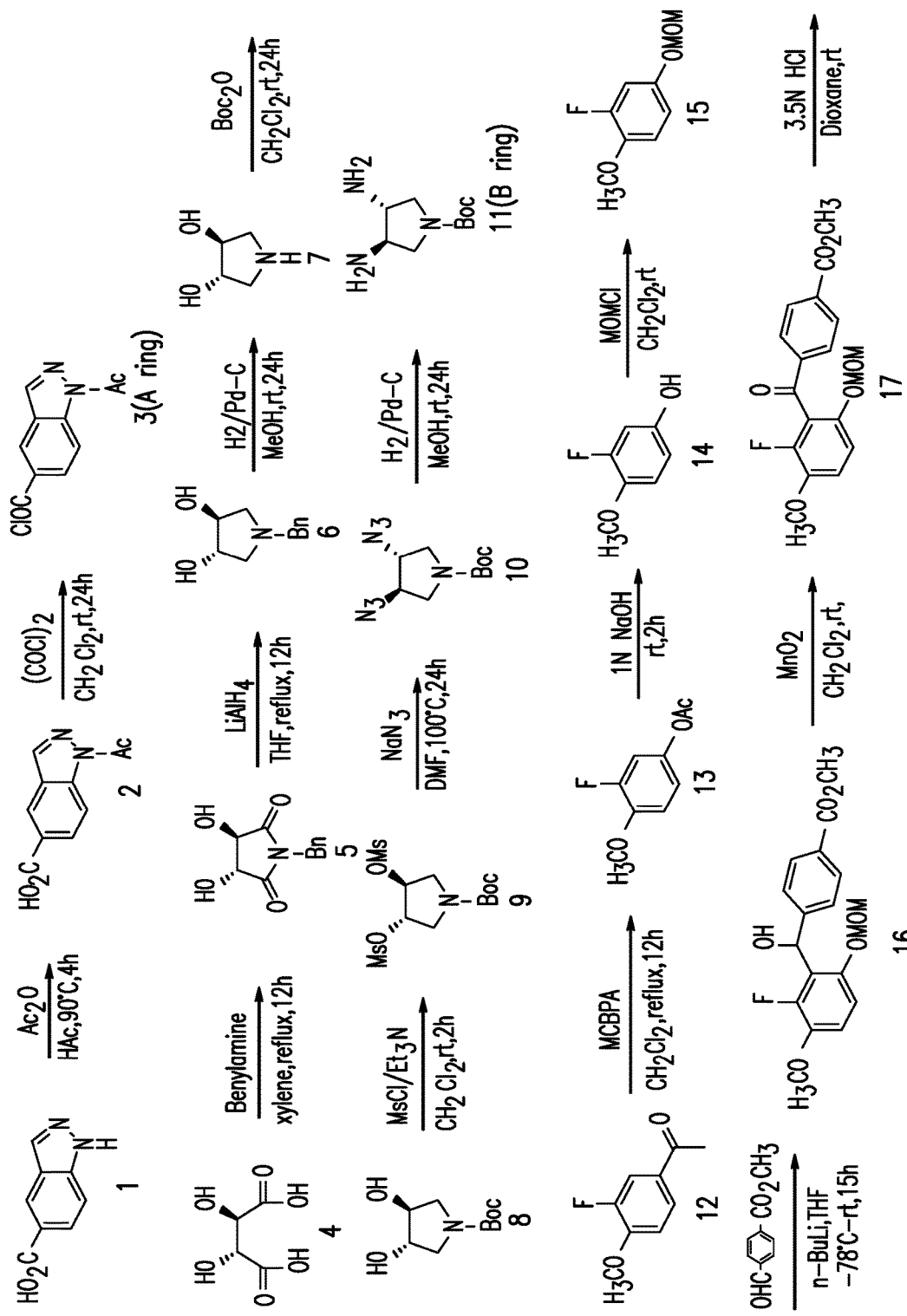
Figure 2:
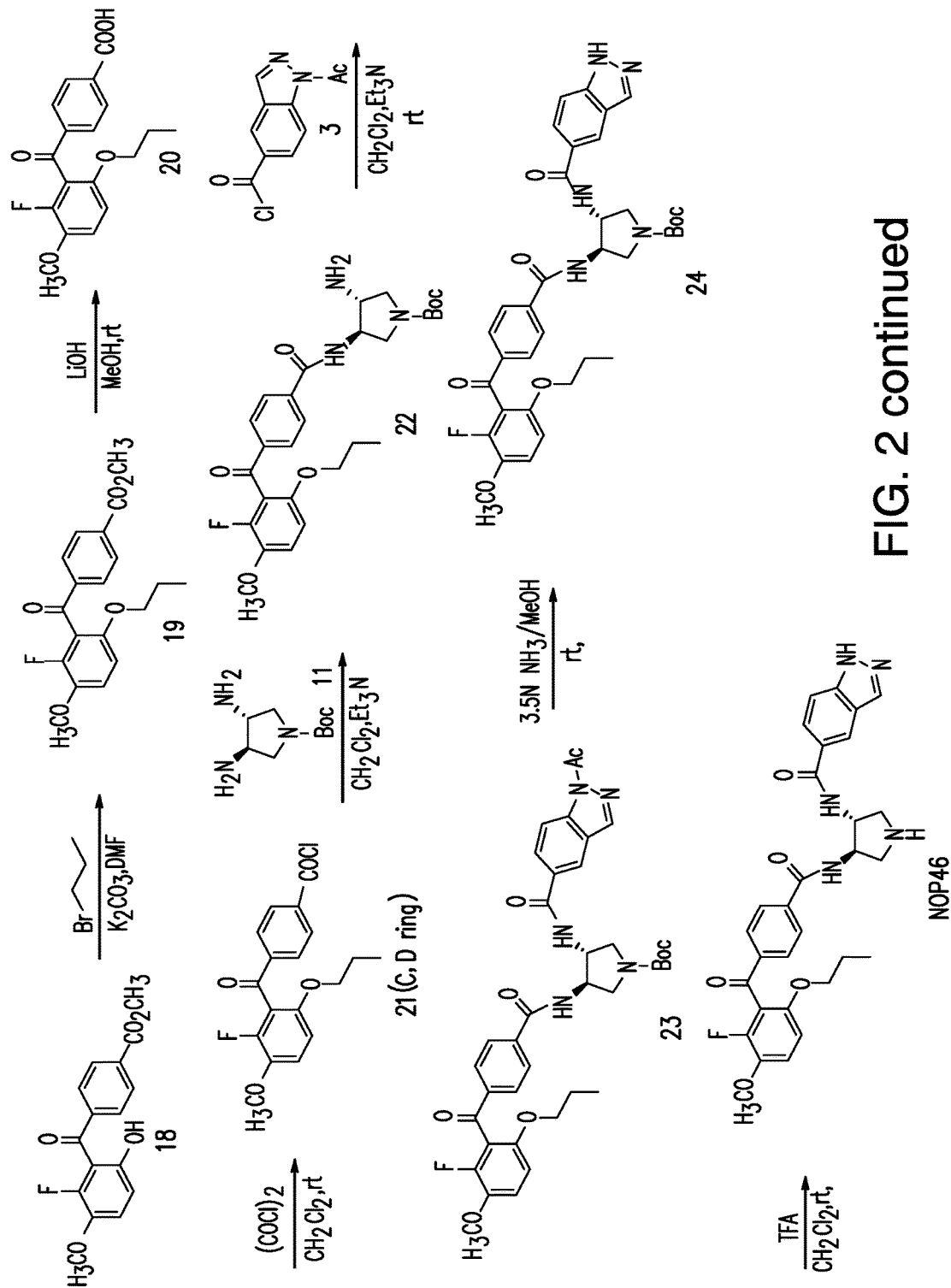

FIG. 2. A synthesis scheme for NOP46.

Figure 3:
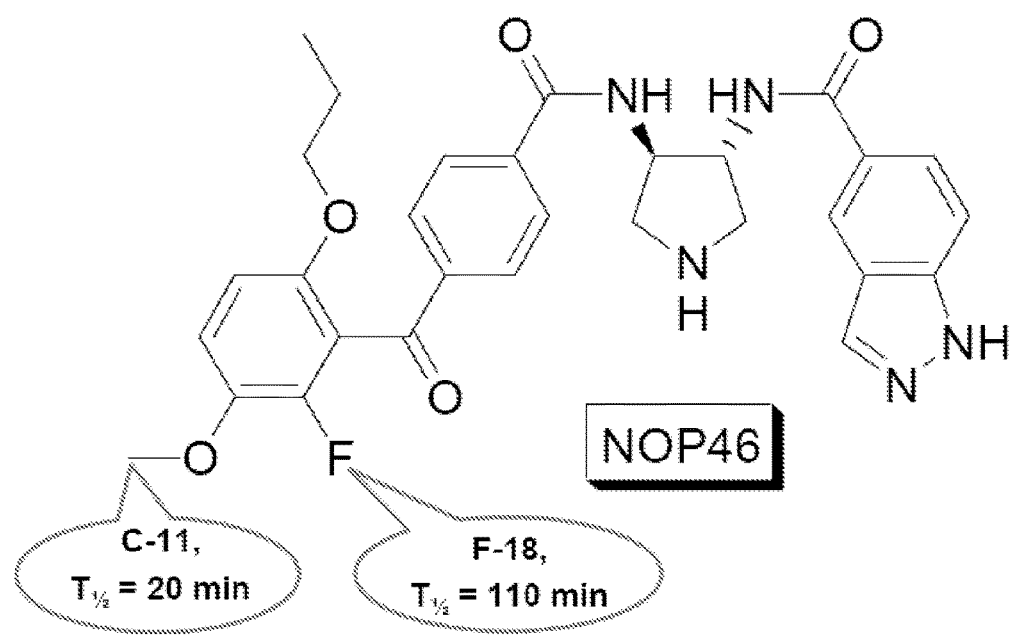

FIG. 3. Potential sites for labeling in NOP46.

FIG. 4. Chemical synthesis scheme using [$^{18}$F].

Figure 5A:
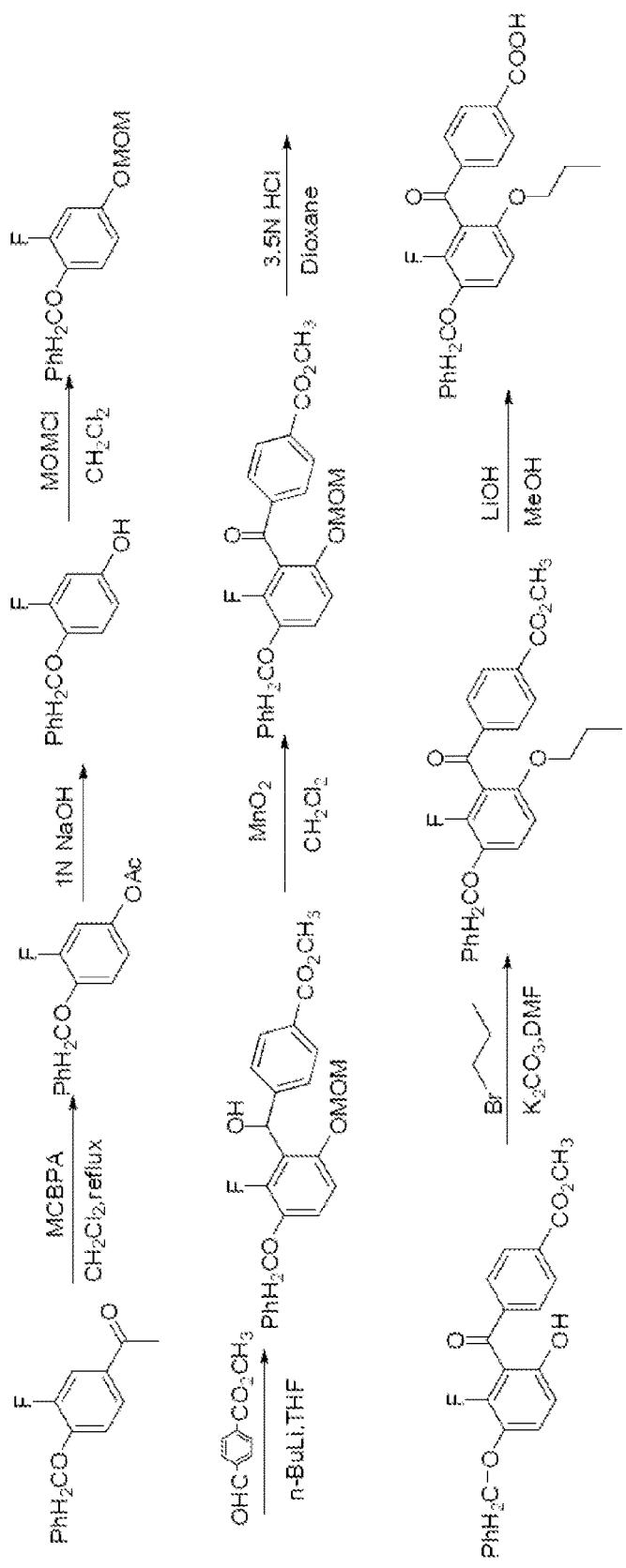
Figure 5A:
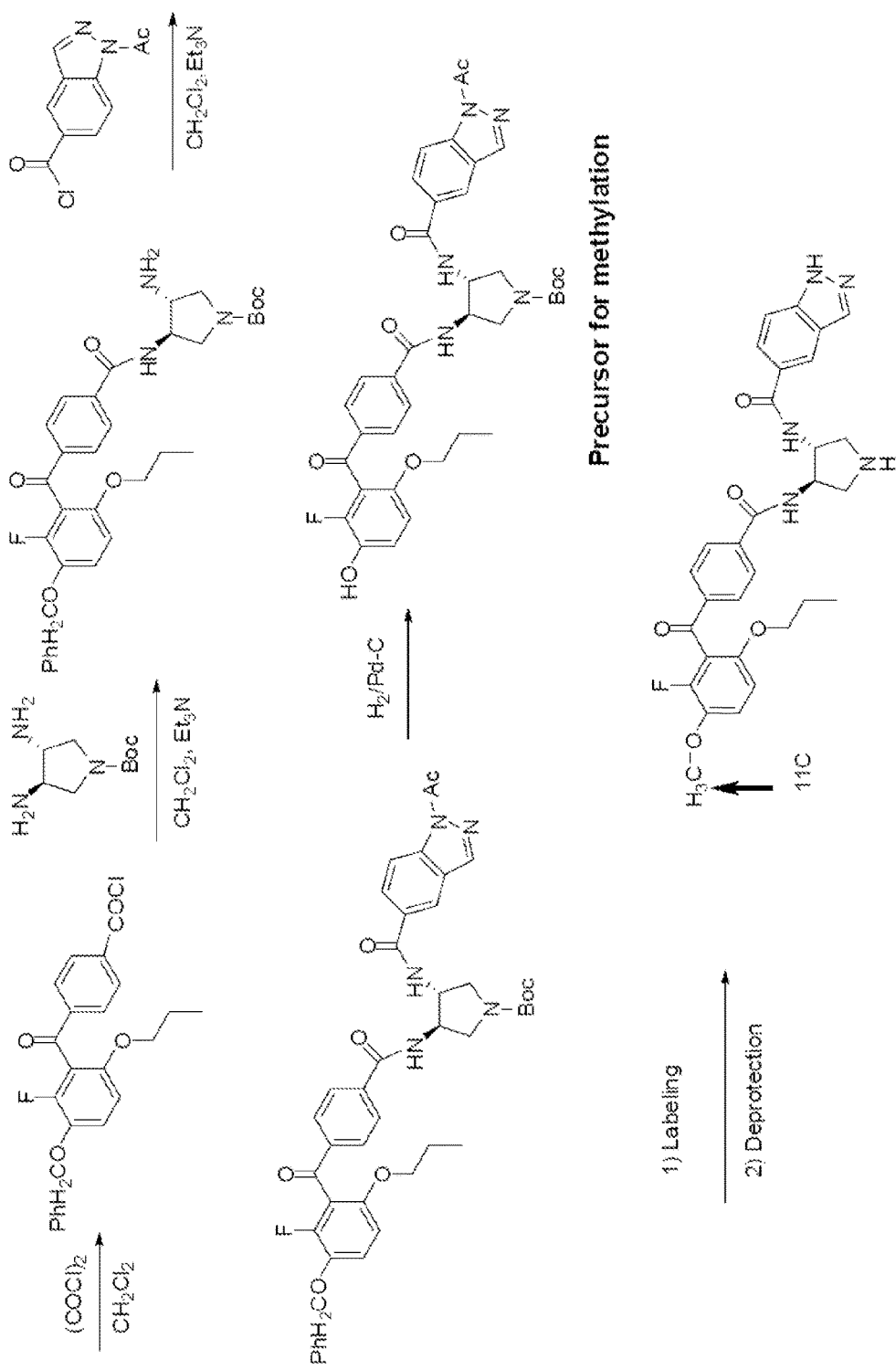
Figure 5B:
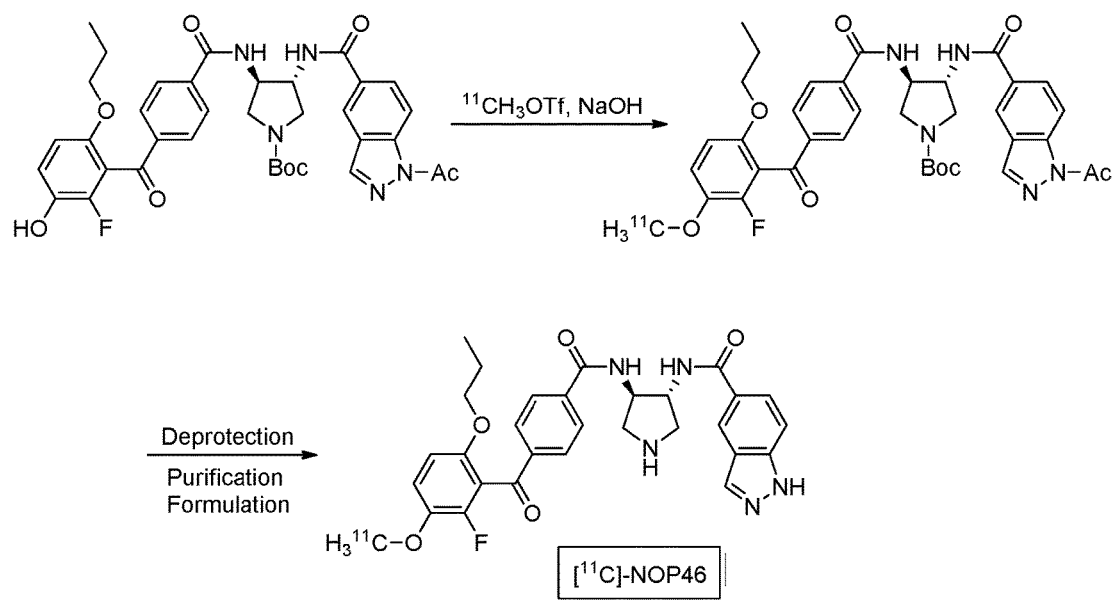

FIG. 5A-B. Chemical synthesis scheme (A) to produce a precursor for carbon isotope labeling and (B) to introduce [$^{11}$C] into NOP46.

Figure 6:
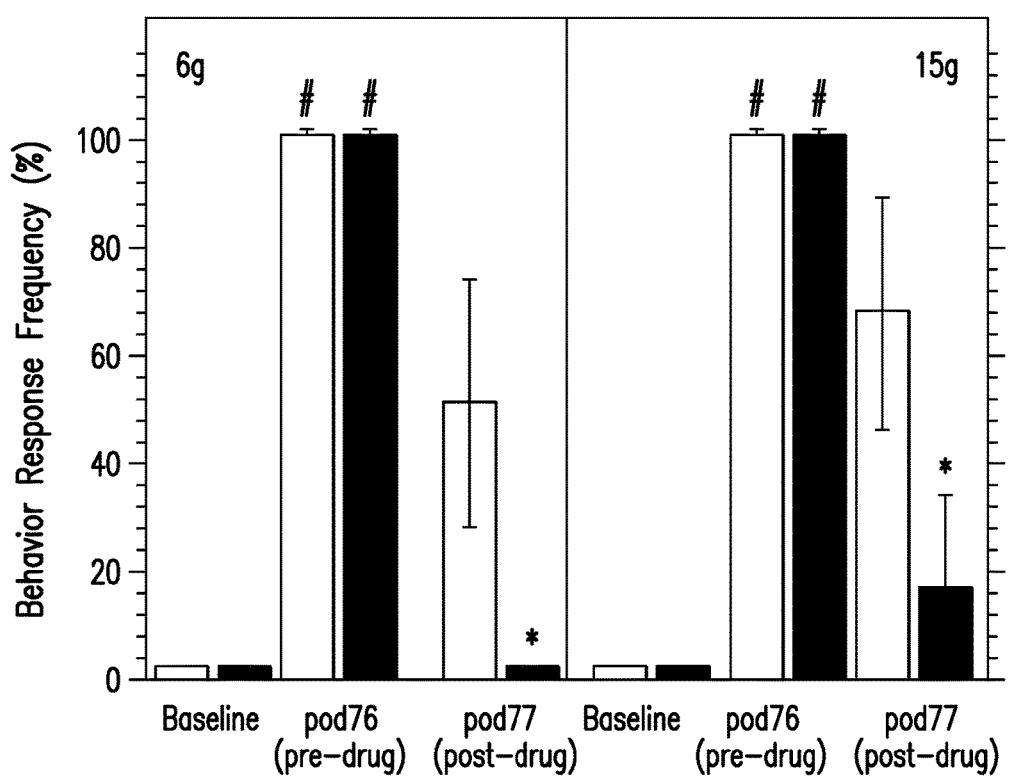

FIG. 6. NOP46 alleviated mechanical allodynia and thermal hyperalgesia in models of chronic pain.

FIG. 7A-B. (A) Exemplary NOP compounds. (B) Exemplary NOP compounds having formula I linked to R.

Figure 8:
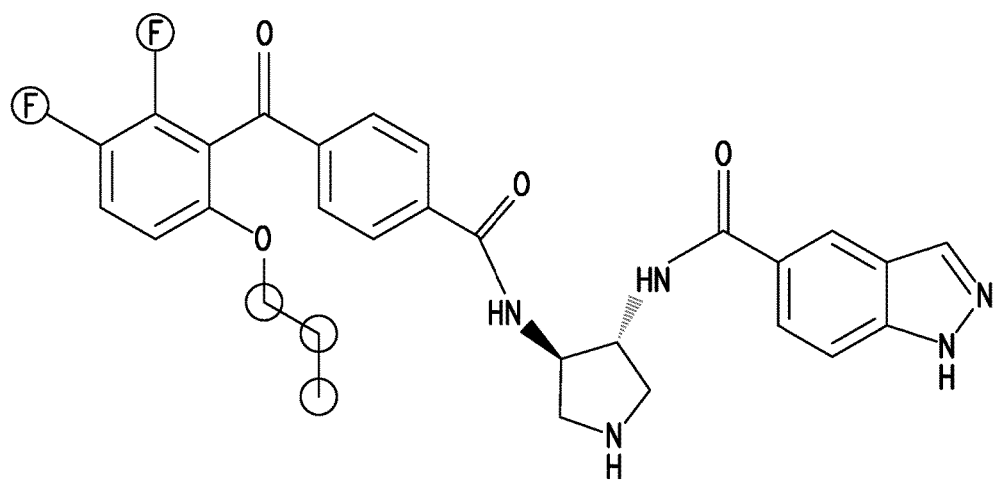

FIG. 8. Potential sites for labeling in NOP60.

Figure 9A:
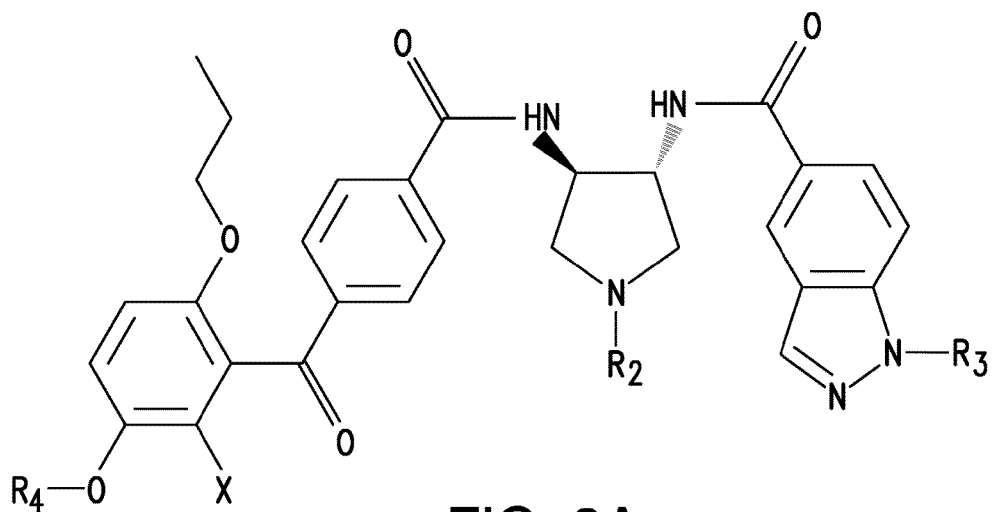
Figure 9B:
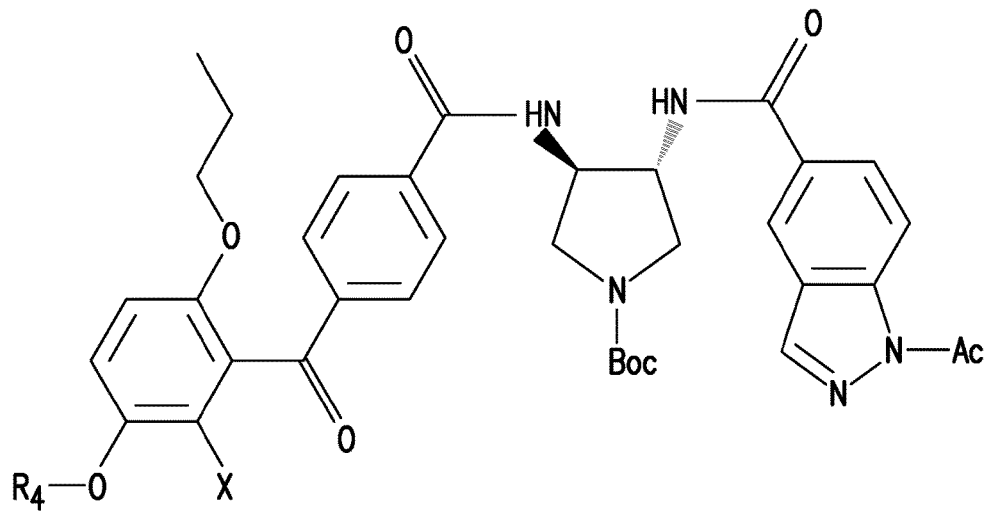

FIG. 9A-B. (A) NOP46 labeling precursor molecule. (B) NOP46 labeling precursor molecule with particular protecting groups.

5. DETAILED DESCRIPTION OF THE INVENTION

For purposes of clarity, and not by way of limitation, the detailed description of the invention is divided into the following subsections:
(i) NOP compounds;
(ii) methods for preparing labeled NOP compounds; and
(iii) pain-imaging methods.

5.1 NOP Compounds

The present invention relates to NOP compounds and analogs thereof which may be used as precursors for producing detectably labeled NOP compounds. FIG. 7A depicts non-limiting examples of NOP compounds which may be used according to the invention. Additional NOP compounds, and synthetic schemes for NOP compounds, are disclosed in United States Patent Application Publication No. 20080176920.

In particular non-limiting embodiments, NOP compounds of the invention have Formula 1:

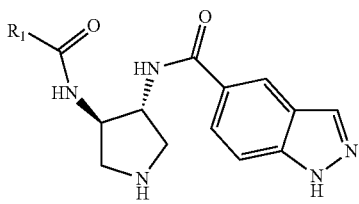

where $R_1$ may be (i) $Ar_1$—(C=O)—$Ar_2$ where $Ar_1$ and $Ar_2$ are each independently substituted or unsubstituted benzyl; (ii) substituted or unsubstituted benzyl; or (iii) substituted or unsubstituted benzopyrazole; where, for (i), (ii) or (iii), substituent(s), if present, may be hydroxy, fluorine, bromine, iodine, $NO_2$, $N^+(CH_3)_4$, $I^+C_4H_6CH_3$-p, $(C_1-C_4)$alkoxy, fluoro($C_1-C_4$)alkoxy, or amino($C_1-C_4$)alkoxy. Specific non-limiting examples having Formula 1 illustrative of non-limiting examples of $R_1$ are shown in FIG. 7B.

NOP46 (FIG. 1A-B) is a small-molecule compound that binds with high affinity and selectivity to an activated form of protein kinase G-1α (PKG-1α) which is present only in DRG whose nociceptive neurons are mediating chronic pain. The IC50 of NOP46 for PKG is 7.5 nM, whereas the IC50 of NOP46 for Protein Kinase A ("PKA") is 2,000 nM. Kinetic analysis shows that NOP46 is a non-competitive inhibitor of the ATP site. Furthermore, NOP46 reaches the DRG within 30 min of injection, is stable within the ganglion for at least 24 h, and does not enter the central nervous system. In one non-limiting embodiment, a synthesis for NOP46 is shown in FIG. 2 and is discussed in the subsection below. To produce radiolabeled NOP46, the synthesis may be modified as discussed below or using methods known in the art.

NOP46 has been observed to be stable in blood in vitro, and is rapidly cleared from the circulation following intravenous injection. Microsome preparations indicated that the compound is degraded by carbonyl reduction and depropylation, consistent with catabolism in the liver, which was confirmed by tissue distribution studies that showed high initial levels of NOP46 in the liver.

In other specific non-limiting embodiments of the invention, NOP60 (FIG. 7B, FIG. 8) may be used. Potential sites of labeling are circled in FIG. 8. For example, and not by way of limitation, either or both of the fluorines may be substituted with [$^{18}$F], or one or more carbon in the alkoxy group may be [$^{11}$C].

In certain non-limiting embodiments, the invention provides for precursor compounds of labeled NOP compounds. In particular non-limiting embodiments, said precursor has Formula II:

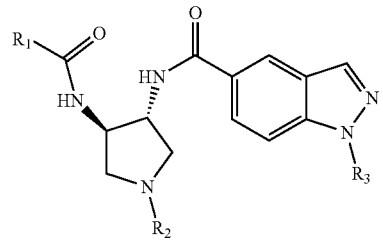

where $R_1$ is as set forth above and $R_2$ and $R_3$ are blocking groups. In non-limiting specific examples, $R_2$ and $R_3$ may be N-tert-butoxycarbonyl ("Boc") or acetyl ("Ac").

In certain non-limiting embodiments, a NOP labeling precursor compound has the structure shown in FIG. 9A, where $R_2$ and $R_3$ are as set forth above, X is either F or, for example where the precursor is for use in preparing a compound labeled at this position, X may be a labeled moiety such as a radioisotope (e.g., $^{18}$F) or a suitable "leaving group" and may be a halogen such as bromine (Br) or iodine (I), a nitro group ($NO_2$), an alkylammonium group (such as $^+N(CH_3)_4$), an aryliodonium group (such as $^+IC_6H_4CH_3$), or any other group that is used in $^{18}$F radiolabeling, and $R_4$ is either methyl, or, for example where the precursor is for use in preparing a compound labeled at this position, $R_4$ may be a methyl group containing a radioisotope (e.g. $^{11}CH_3$) or H (to form a hydroxyl group), or a cation (such as $Li^+$, $Na^+$, $K^+$, $Cs^+$, or $NH_4^+$. A specific non-limiting example of a precursor of labeled NOP46 is shown in FIG. 9B, where X and $R_4$ are as set forth above. Non-limiting examples of NOP46 labeling precursors and labeled NOP46 are shown in FIGS. 4 and 5.

Additional labels that may be incorporated into NOP compounds of formula I include, but are not limited to, $^{18}$F-fluoroalkyl (for example $^{18}$FCH$_2$, $^{18}$FCD$_2$, $^{18}$FCH$_2$CH$_2$) or radiohalogens (for example, $^{76}$Br or $^{123/125}$I). In specific non-limiting example, a $^{18}$F fluoroalkyl may be R$_4$ in the formulas depicted in FIG. 9A and 9B, or radiohalogen may be X in the formulas depicted in FIG. 9A and 9B.

5.1.1 Synthesis of NOP46

In one specific non-limiting embodiment, NOP46 may be synthesized using a method exemplified as follows (see FIG. 2):

Part 1. Synthesis of A Ring (3)
1.1 1-acetyl-1H-indazole-5-carboxylic acid (2)

A solution of 1.62 g of compound 1 in 5 mL of acetic anhydride and 5 mL of acetic acid was heated to 90° C. with stirring for 4 h. The reaction mixture was cooled and concentrated to give 2.02 g of compound 2 as a white powder, which was used without further purification.

1.2 1-acetyl-1H-indazole-5-carbonyl chloride (3)

To a solution of 1.90 g of compound 2 and 5 mL of oxalyl chloride in 10 mL of methylene chloride was added 1 drop of DMF. The mixture was stirred at rt for 24 h and concentrated to give 2.06 g of compound 3 as a white powder, which was used without further purification.

Part 2. Synthesis of B Ring (11)
2.1 (3R,4R)-tert-butyl 3,4-diaminopyrrolidine-1-carboxylate (11)

Compound 11 was made according to *Angewandte Chemie, International Edition*, 41(20), 3852-3854, 2002 and *Synthetic Communications*, 38(14), 2374-2384, 2008. The intermediate 8 is also commercially available at AB Chem, Inc. 2286 Ch. St-Francois, Dorval, H9P 1K2. Tel: 514-685-8688 Fax: 514-685-8488. We bought 200 g from the company.

Part 3. Synthesis of C, D Ring (21)
3.1 acetic acid 3-fluoro-4-methoxy phenyl ester (13)

A mixture of 25 g (0.15 mol) of 3-fluoro-4-methoxyacetophenone (12) and 40 g (0.2 mol) of 85% 3-chloroperoxybenzoic acid in 350 ml of methylene chloride was refluxed for 48 h, cooled and washed with 5% potassium carbonate solution (200 ml) three times. The organic phase was dried with MgSO$_4$ and the solvent was evaporated. The crude product (24 g, 87.0%) was used for the next step without further purification.

3.2 3-fluoro-4-methoxyphenol (14)

20 g of 13 (0.11 mol) obtained above was dissolved in 200 ml of ethanol and 100 ml of 20% NaOH solution was added slowly. The resulting reaction mixture was stirred for 3 h at room temperature. The aqueous solution was washed with ether and acidified with 6N HCl. The oil which separated was extracted into ether and the extracts were dried with MgSO$_4$. Removal of the solvent left a solid residue which was recrystallized from hexane to give 13 g product (83.3%)

3.3 2-fluoro-1-methoxy-4-methoxymethoxy-benzene (15)

A mixture of 3.0 g (21 mmol) of 14 and 7 ml of N,N-diisopropylethylamine (73 mmol) was dissolved in 100 ml of methylene chloride. To this solution cooled with ice-water bath, 0.3 ml of chloromethyl methyl ether (39.5 mmol) was added dropwise. After addition, the reaction mixture was stirred at room temperature for 3 h. After removing solvent, the residue was purified by chromatography on silica gel (elute with methylene chloride) to give 3.9 g product as light yellow oil (100%).

3.4 4-[(2-fluoro-3-methoxy-6-methoxymethoxy-phenyl)-hydroxy-methyl]-benzoic acid methyl ester (16)

10 ml of 1.6 M of n-BuLi in THF (16 mmol) was added slowly to 2.5 g of 15 (13.4 mmole) in 50 ml of dry THF at −78° C. The solution was stirred at the same temperature for 40 minutes. To this solution, a solution of 2.2 g of 4-Formylbenzoic acid methyl ester (13.4 mmol) in 50 ml of dry THF was added by canal slowly(internal temperature was kept under −65° C.). The reaction was stirred at −65° C. for 6 h and the reaction was allowed to warm up to room temperature in 15 h. The reaction was quenched with water and extracted with ethyl acetate (100 ml) three times. The combined organic phases were dried with MgSO$_4$. After removing solvent, the residue was purified by chromatography on silica gel (elutes with ethyl acetate:hexane=4:6) to give 3.1 g of product as yellow oil (66.0%).

3.5 4-(2-fluoro-6-hydroxymethoxy-3-methoxy-benzoyl)-benzoic acid methyl ester (17)

2.0 g of 16 (5.7mmole) was dissolved in 50 ml of methylene chloride and to this solution, 15 g of activated MnO$_2$ was added in portions. The reaction was stirred at room temperature overnight. The solution was filtered through a celite pat and after removing the solvent, 1.7 g of product was obtained as yellow oil (86%).

3.6 methyl 4-(2-fluoro-6-hydroxy-3-methoxybenzoyl)benzoate (18)

1.5 g of 17 (4.3 mmol) was dissolved in 10 mL of dioxane and to this solution, 5 mL of 4 M HCl dioxan solution was added. The reaction mixture was stirred at rt overnight. The solvent was removed to get 1.3 g of yellow crystal (100%).

3.7 methyl 4-(2-fluoro-3-methoxy-6-propoxybenzoyl)benzoate (19)

A mixture of 1.2 g of 18 (4.0 mmol), 0.91 mL of 1-bromopropane (10 mmol) and 1.66 g of potassium carbonate in 5 mL of DMF was stirred at rt overnight. After removing the solvent, the residue was dissolved in 50 mL of ethyl ether and washed with 10 mL of water for 3 times. The organic was dried with MgSO$_4$ and concentrated to give 1.3 g of light yellow oil (95%).

3.8 4-(2-fluoro-3-methoxy-6-propoxybenzoyl)benzoic acid (20)

1.2 g of 19 (3.5 mmol) was dissolved in 15 ml of methanol and water was added dropwise until the solution became cloudy. 1.0 g of LiOH (2.4 mmol) was added slowly and the reaction was stirred at room temperature overnight. The reaction was quenched with 7.0 g of citric acid. After removing most of methanol, the aqueous solution was extracted with methylene chloride (30 ml) three times and combined organics was washed with brine twice, dried (MgSO$_4$). 1.1 g of product was obtained as white solid after removal of the solvent (95%).

3.9 4-(2-fluoro-3-methoxy-6-propoxybenzoyl)benzoyl chloride (21)

To a solution of 1.0 g of compound 20 (3.0 mmol) and 2 mL of oxalyl chloride in 5 mL of methylene chloride was added 1 drop of DMF. The mixture was stirred at rt for 24 h and concentrated to give 1.05 g of compound 21 as a white powder, which was used for the next reaction without further purification.

Part 4. Synthesis of NOP46
4.1 (3R,4R)-tert-butyl 3-amino-4-(4-(2-fluoro-3-methoxy-6-propoxybenzoyl)benzamido)pyrrolidine-1-carboxylate (22)

To a solution of 200 mg of 11 (1 mmol), 0.5 mL of triethylamine (3.6 mmol) in 10 mL of methylene chloride, was added a solution of 350 mg of 21 in 5 mL of methylene chloride dropwise. After addition, the reaction was stirred at room temperature for 3 h. After removing solvent, the residue was purified by chromatography on silica gel (elute with ethyl acetate:methanol=6:1) to give 180 mg product as white powder (35%).

4.2 (3R,4R)-tert-butyl 3-(1-acetyl-1H-indazole-5-carboxamido)-4-(4-(2-fluoro-3-methoxy-6-propoxybenzoyl)benzamido)pyrrolidine-1-carboxylate (23)

To a solution of 155 mg of 22 (0.3 mmol), 0.2 mL of triethylamine (1.4 mmol) in 5 mL of methylene chloride, was added a solution of 90 mg of 3 (0.4 mmol) in 2 mL of methylene chloride. After addition, the reaction was stirred at room temperature for 3h. After removing solvent, the residue was purified by chromatography on silica gel (elute with ethyl acetate:methylene chloride=1:1) to give 170 mg product as white powder (80%).

4.3 N-((3R,4R)-4-(4-(2-fluoro-3-methoxy-6-propoxybenzoyl)benzamido)pyrrolidin-3-yl)-1H-indazole-5-carboxamide (NOP46)

2 mL of 7N ammonia in methanol was added to a solution of 150 mg of 23 (0.21 mmol) in 2 mL of methanol, the reaction mixture was stirred at rt overnight. The solvent was removed to get 24 as white powder, which was added 2 mL of methylene chloride and 1 mL of TFA and stirred at rt for 3 h. The solvent was removed to get 166 mg product (NOP46) as white powder (100%).

5.2 Methods for Preparing Labeled NOP Compounds

5.2.1 $^{18}$F-Labeled NOP Compounds

A non-limiting example of a scheme for making $^{18}$F labeled NOP46 is shown in FIG. 4. An analogous method could be used to produce $^{18}$F-NOP60 or other NOP compounds containing a fluorine atom. Radiolabeling may be carried out using well-established [$^{18}$F]fluoroaromatic chemistry methods. In a specific non-limiting embodiment, $^{18}$F-NOP46 may be prepared by reacting a radiolabeling precursor with [$^{18}$F]fluoride in the presence of, for example, Kryptofix 222 followed by the removal of the N-Boc and N-acetyl protecting groups from the resulting radiolabeled intermediate (FIG. 4). In non-limiting embodiments, [$^{18}$F] fluoride may be produced from oxygen-18 enriched water via the $^{18}$O(p,n)$^{18}$F nuclear reaction. The radiolabeling precursor may be obtained, for example, but not by way of limitation, by methods described in United States Patent Application Publication No. 20080176920. The precursor and [$^{18}$F]Fluoride may be reacted in a commonly used reaction solvent such as, but not limited to, dimethylsulfoxide or acetonitrile).

5.2.2 $^{11}$C-Labeled NOP Compounds

In certain non-limiting embodiments of the invention, $^{11}$C is placed at the site of a carbon atom in a NOP structure.

In one specific non-limiting embodiment, $^{11}$C is incorporated into the methoxy group of NOP46. The NOP46 molecule contains a methoxy group where carbon-11 can be readily introduced without any changes in the structure (and thus, in the physicochemical or biological properties) whatsoever. Radiolabeling may be carried out using well established [$^{11}$C]-methyl chemistry methods. In a specific non-limiting embodiment, $^{11}$C-NOP46 may be prepared by reacting a radiolabeling precursor (O-Desmethyl-N-Boc-N acetyl-NOP46, which may be prepared, for example, as set forth in FIG. 5A) with a [$^{11}$C]-methylating agent (such as [$^{11}$C] methyl iodide or [$^{11}$C]methyl triflate) followed by the removal of the N-Boc and N-acetyl protecting groups from the resulting radiolabeled intermediate (FIG. 5B). [$^{11}$C] Methyl iodide or [$^{11}$C] methyl triflate may be prepared from [$^{11}$C]CO$_2$, produced via the $^{14}$N(p,α)$^{11}$C nuclear reaction, by the "dry method" according to the following reaction sequence: [$^{11}$C]CO2→[$^{11}$C]CH$_4$→[$^{11}$C]CH$_3$I→[$^{11}$C] CH$_3$OTf. The radiolabeling desmethyl precursor may be obtained by the methods developed previously (see United States Patent Application Publication No. 20080176920. The precursor and [$^{11}$C]methyl iodide or triflate may be reacted in a commonly used reaction solvent (such as acetone, methyl ethyl ketone) in the presence of a base (such as sodium hydroxide).

5.2.3 Deprotection and Purification

The deprotection step may be performed using traditional agents, such as trifluoroacetic or hydrochloric acid.

After the preparation, labeled NOP compound may be purified by means of reverse-phase high performance liquid chromatography (HPLC), isolated on a solid-phase extraction cartridge, formulated as a sterile non-pyrogenic solution, and subjected to a battery of quality control tests prior to release for administration. Quality control tests may be performed to ensure that the labeled compound meets all applicable identity, purity, and safety criteria, and may include the following analyses: examination of visual appearance, sterilizing filter integrity test, pH measurement, radionuclidic identity determination, radionuclidic purity measurement, radiochemical purity determination, radioactivity concentration measurement, chemical identity verification, drug mass concentration determination, specific activity calculations, individual and total chemical impurities concentration measurements, residual solvents concentration determination, pyrogen content measurement, and sterility determination.

5.3 Pain Imaging Methods

In a non-limiting embodiment, the present invention provides for a method of identifying a dorsal root ganglion associated with pain in a subject, comprising administering, to the subject, a detectable amount of detectably labeled NOP compound, and then detecting labeled NOP compound that has localized in the dorsal root ganglion.

In a related embodiment, the present invention provides for a method of quantifying the level of pain in a subject, comprising administering, to the subject, a detectable amount of detectably labeled NOP compound, and then quantifying the amount of labeled NOP compound that has localized in the dorsal root ganglion and/or comparing that level to a control value.

The subject may be a human or a non-human subject such as a non-human primate, a canine, a feline, a horse, a pig, a cow, a sheep, a goat, a rodent, a rabbit, a guinea pig, a bird, a cetacean, etc. The subject may complain of or act in a manner consistent with the experience of pain.

Detectably labeled NOP compounds are set forth above.

Methods of detecting labeled NOP include, but are not limited to, positron emission tomography ("PET") and single photon emission computed tomography ("SPECT").

A detectable amount is an amount which is detectable in a subject experiencing a medium level of pain. The amount of labeled NOP compound administered may be adjusted to reflect the specific activity of label. In particular non-limiting embodiments, the amount of [$^{18}$F] or [$^{11}$C]-NOP administered may be for [$^{18}$F]-NOP 5-10 mCi (185-370 MBq) or 5-15 mCi (185-555 MBq) or 5 MBq/kg and for [$^{11}$C]-NOP, 10-20 mCi (370-740 MBq).

In a specific, non-limiting embodiment, where [$^{18}$F] or [$^{11}$C]-NOP46 is used, the following protocol or a modification thereof may be practiced:

(i) Prior to the PET study, a neurologic examination including identification of putatively involved dorsal root ganglia, as well as a VAS test for pain, may be performed.

(ii) The subject may be asked to void urine (& stool, as appropriate) prior to the study.

(iii). PET imaging may be performed on a PET or PET/CT scanner, after intravenous injection of labeled-NOP46.

(iv). Serial whole body images of the body may be obtained starting immediately after injection and at regular intervals subsequently for no more than 4 hours.

(v). Data may be reconstructed according to standard methods for clinical interpretation, and analyzed using OLINDA for radiation dose to the body and critical organs.

(vi) Images may be analyzed for any evidence of unexpected biodistribution and or targeting to putatively involved dorsal root ganglia.

Images obtained from subjects experiencing pain may be compared to images from pain-free subjects to establish a control value and positive values.

6. EXAMPLE 1

NOP46 selectively inhibits activated PKG1alpha. Its kinase inhibiting activity was assayed in 287 kinases at their optimal ATP concentrations. Members of all the kinome families were represented. Table 1 below shows the fold-inhibition by NOP46.

TABLE 1

| Kinase | Inhibition of control activity |
|---|---|
| MRCK(h) | 0 |
| MuSK(h) | −1 |
| PKA(h) | 1 |
| PKB beta | 1 |
| PKG1alpha(h) | −6 |
| PRK2(h) | −1 |
| PrKX(h) | 1 |
| ROCK-II(r) | −1 |
| SGK(h) | 1 |

7. EXAMPLE 2

When injected into rats, NOP46 alleviated mechanical allodynia and thermal hyperalgesia in models of chronic pain (FIG. 6). Evaluation of neuroma pain was made possible with the advent of a novel protocol in rats whereby the end of a transected tibial nerve is transposed and then anchored just beneath the skin of the ankle [14]. This allows the allodynia from the neuroma to be evaluated by systematically applying pressure to the overlying skin and observing whether the rat raises the leg. PKG-1α is active in the DRG in painful neuromas and the finding that NOP46 alleviates neuroma pain indicates that there is targeting of the ligand to the PKG-1α.

8. REFERENCES

1. Centers for Disease Control and Prevention. 2012. CDC Grand Rounds: Prescription Drug Overdoses—a U.S. Epidemic. Morbidity and Mortality Weekly Report 61:10-13. Available at http://www.cdc.gov/mmwr/pdf/wk/mm6101.pdf. Accessed Jan. 27, 2013.

2. Centers for Disease Control and Prevention. 2011. Vital Signs: Overdoses of Prescription Opioid Pain Relievers—United States, 1999-2008. Morbidity and Mortality Weekly Report 60:1487-1492. Available at http://www-.cdc.gov/mmwr/pdf/wk/mm6043.pdf. Accessed Jan. 27, 2013.

3. Centers for Disease Control and Prevention. 2011. Policy Impact: Prescription Painkiller Overdoses. Atlanta, Ga.: US Department of Health and Human Services, CDC. Available at http://www.cdc.gov/homeandrecreationalsafety/rxbrief/index.html. Accessed Jan. 27, 2013.

4. Committee on Advancing Pain Research, Care, and Education, Institute of Medicine. 2011. Relieving Pain in America: A Blueprint for Transforming Prevention, Care, Education and Research. Washington, D.C.: The National Academies Press. Available at http://www.nap.edu/catalog.php?record_id=13172. Accessed Jan. 27, 2013.

5. Jamison, R. N., Serraillier, J., and Michna, E. 2011. Assessment and treatment of abuse risk in opioid prescribing for chronic pain. Pain Research and Treatment 2011: Article ID 941808. Available at http://www.hindawi.com/journals/prt/2011/941808. Accessed Jan. 27, 2013.

6. Pasero, C. and McCaffery, M. 1999. Pain: Clinical Manual. St. Louis: Mosby.

7. Sherman, R. A., Tan, G., and Shanti, B. F. 2004. Thermography in Pain Management. Prac-tical Pain Management 4. Available at http://www.practicalpainmanagement.com/resources/diagnostic-tests/thermography-pain-management. Accessed Jan. 27, 2013.

8. Sung, Y. J. and Ambron, R. T. 2004. Pathways that elicit long-term changes in gene ex-pression in nociceptive neurons following nerve injury: contributions to neuropathic pain. Neurological Research 26:195-203. PMID15072639.

9. Voscopoulos, C. and Lema, M. 2010. When does acute pain become chronic? British Journal of Anaesthesia 105 (S1): i69-i85. Available at http://bja.oxfordjournals.org/content/105/suppl_1/i69.full.pdf+html. Accessed Jan. 27, 2013.

10. Sung, Y. J., Chiu, D. T. W., and Ambron, R. T. 2006. Activation and retrograde transport of protein kinase G in rat nociceptive neurons after nerve injury and inflammation. Neuroscience 141:697-709. PMID16730916.

11. Caraceni, A., Martini, C., Zecca, E. and Fagnoni E. 2012. Cancer pain management and palliative care. Handbook of Clinical Neurology 104:391-415.

12. Montazeri A. 2009. Quality of life data as prognostic indicators of survival in cancer patients: an overview of the literature from 1982 to 2008. Health and Quality of Life Outcomes 7:102-123.

13. Raphael, J., Ahmedzai, S., Hester, J. et al. 2010. Pain: Part 1: Pathophysiology; Oncological, Pharmacological and Psychological Treatments: A Perspective from the British Pain Society Endorsed by the UK Association of Palliative Medicine and the Royal College of General Practitioners. Pain Med. 11:742-764.

14. Dorsi, M. J., Chen, L., Murinson, B. B. et al., 2008. The tibial neuroma transposition (TNT) model of neuroma pain and hyperalgesia. Pain 134:320-334.

Various publications are cited herein, the contents of which are hereby incorporated by reference in their entireties.

What is claimed is:

1. Radiolabeled NOP46 having the chemical structures

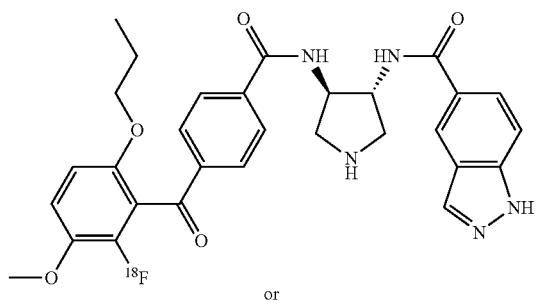

or

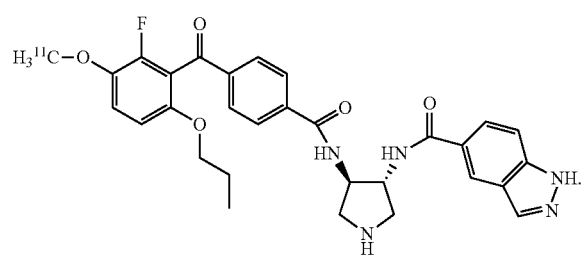

2. A pharmaceutical composition comprising radiolabeled NOP46 having the structures

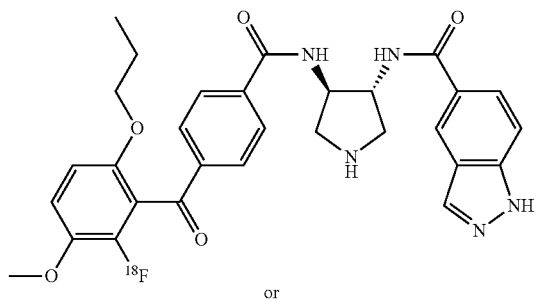

or

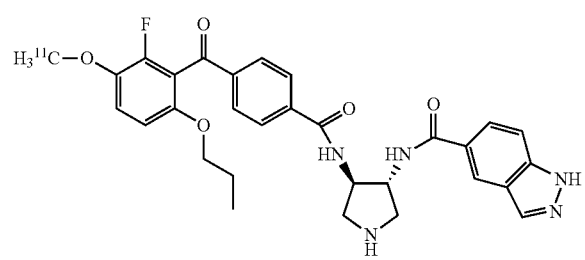

wherein the radiolabeled NOP46 is in an amount detectable by positron emission tomography or single photon emission computed tomography.

3. A method of identifying a dorsal root ganglion associated with pain in a subject, comprising administering, to the subject, a detectable amount of detectably labeled NOP compound comprising a radioisotope, and then detecting the labeled NOP compound that has localized in the dorsal root ganglion, where the detectably labeled NOP compound is radiolabeled NOP46 having the structures

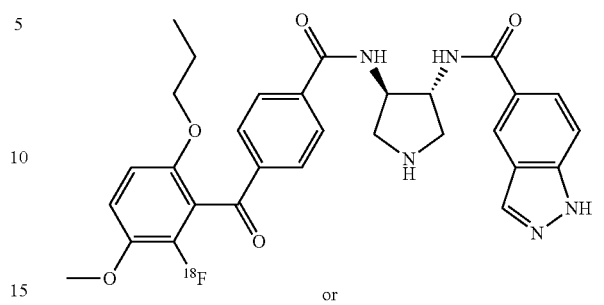

or

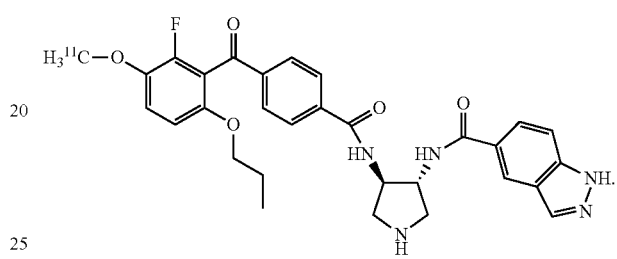

4. A method of quantifying the level of pain in a subject, comprising administering, to the subject, a detectable amount of detectably labeled NOP compound comprising a radioisotope, and then quantifying the amount of labeled NOP compound that has localized in the dorsal root ganglion and/or comparing that level to a control value, where the detectably labeled NOP compound is radiolabeled NOP46 having the structures

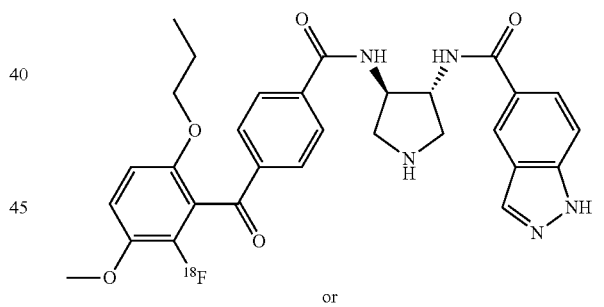

or

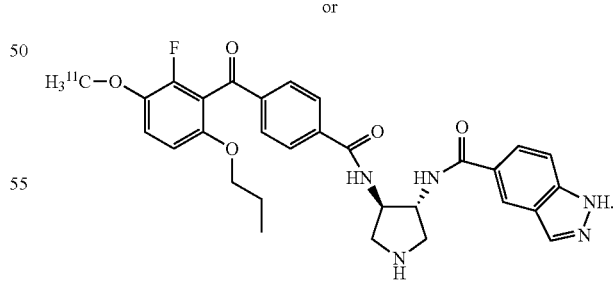

* * * * *